United States Patent [19]
Yabe et al.

[11] Patent Number: 5,460,166
[45] Date of Patent: Oct. 24, 1995

[54] ENDOSCOPE OF AN ENDOSCOPE COVER SYSTEM WHEREIN, AT THE TIME OF THE MAXIMUM CURVATURE, A FLUID TUBE PATH WILL BE CURVED AS TWISTED SO AS TO MOVE TO THE SIDE ON WHICH THE RADIUS OF CURVATURE WILL BECOME LARGER

[75] Inventors: Hisao Yabe, Hachioji; Yoshihiro Iida, Tama; Akira Suzuki; Hideo Ito, both of Hachioji; Yoshio Tashiro, Hino; Minoru Yamazaki, Hachioji; Osamu Tamada, Hachioji; Motokazu Nakamura, Hachioji, all of Japan

[73] Assignee: Olympus Optical, Ltd., Tokyo, Japan

[21] Appl. No.: 37,100

[22] Filed: Mar. 25, 1993

[30] Foreign Application Priority Data

Mar. 11, 1993 [JP] Japan .................. 5-010481 U
Mar. 11, 1993 [JP] Japan .................. 5-010482 U
Mar. 11, 1993 [JP] Japan .................. 5-010483 U

[51] Int. Cl.$^6$ ...................................... A61B 1/00
[52] U.S. Cl. .................. 600/121; 600/109; 600/146; 600/139
[58] Field of Search ................ 128/4, 6, 844, 128/917, 918, 919

[56] References Cited

U.S. PATENT DOCUMENTS

| | | |
|---|---|---|
| Re. 34,110 | 9/1992 | Opie . |
| 3,162,190 | 12/1964 | Del Gizzo . |
| 4,646,722 | 3/1987 | Silverstein ............. 128/4 |
| 4,721,097 | 1/1988 | D'Amelio ............... 128/4 |
| 4,741,326 | 5/1988 | Sidall .................... 128/4 |
| 4,825,850 | 5/1989 | Opie ...................... 128/4 |
| 4,869,238 | 9/1989 | Opie ...................... 128/6 |
| 4,886,049 | 12/1989 | Darras ................... 128/4 |
| 4,907,395 | 3/1990 | Opie ...................... 53/434 |
| 4,991,564 | 2/1991 | Takahashi .............. 128/4 |
| 4,991,565 | 2/1991 | Takahashi .............. 128/4 |
| 4,997,084 | 3/1991 | Opie ...................... 206/364 |
| 5,050,585 | 9/1991 | Takahashi .............. 128/4 |
| 5,058,567 | 10/1991 | Takahashi .............. 128/4 |

FOREIGN PATENT DOCUMENTS

| | | |
|---|---|---|
| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |

(List continued on next page.)

Primary Examiner—Richard J. Apley
Assistant Examiner—Beverly M. Flanagan
Attorney, Agent, or Firm—Armstrong, Westerman, Hattori, McLeland & Naughton

[57] ABSTRACT

An endoscope cover system endoscope to be used in an endoscope inspection including an endoscope having an elongate inserted part provided with a curvable curving part and an operating part provided with a curving operating knob curving operating the curving part and a channeled endoscope cover having an inserted part cover provided with an endoscope inserting channel through which the inserted part is inserted and such fluid tube path through which a fluid flows as an air feeding tube path so that, when the curving part is curved close to the maximum curvature angle in the maximum curvature angle direction by operating the curving operating knob, the fluid tube path within the inserted part cover will be curved and twisted to move outside in the maximum curvature angle direction.

13 Claims, 23 Drawing Sheets

FOREIGN PATENT DOCUMENTS

| | | |
|---|---|---|
| 2-54734 | 11/1990 | Japan . |
| 3-13105 | 2/1991 | Japan . |
| 3-37030 | 2/1991 | Japan . |
| 3-37029 | 2/1991 | Japan . |
| 3-29635 | 2/1991 | Japan . |
| 3-29634 | 2/1991 | Japan . |
| 3-221024 | 9/1991 | Japan . |
| 3-101906 | 10/1991 | Japan . |
| 3-101907 | 10/1991 | Japan . |
| 3-101905 | 10/1991 | Japan . |
| 3-101904 | 10/1991 | Japan . |
| 3-101903 | 10/1991 | Japan . |
| 3-101902 | 10/1991 | Japan . |
| 3-101901 | 10/1991 | Japan . |
| 4-325138 | 11/1992 | Japan . |

ENDOSCOPE OF AN ENDOSCOPE COVER SYSTEM WHEREIN, AT THE TIME OF THE MAXIMUM CURVATURE, A FLUID TUBE PATH WILL BE CURVED AS TWISTED SO AS TO MOVE TO THE SIDE ON WHICH THE RADIUS OF CURVATURE WILL BECOME LARGER

BACKGROUND OF THE INVENTION

1. Field of the Invention

This invention relates to an endoscope in an endoscope cover system comprising an endoscope for a cover, an endoscope inserting channel through which this cover endoscope is inserted and a channel fitted endoscope cover provided with a fluid channel through which a fluid passes so that, at the time of the maximum curvature, a fluid tube path will be curved and twisted so as to move to the side on which the radius of curvature is larger.

2. Description of the Related Art

It is necessary in an endoscope inspection to use a clean endoscope washed and sterilized before the inspection. A repeatedly used type endoscope in which the inserted part is washed and sterilized before the use and a used and abandoned type endoscope cover system endoscope in which the inserted part is replaced after the inspection have been previously suggested.

As disclosed, for example, in U.S. Pat. No. 4,991,564, the endoscope cover system endoscope comprises a combination of an endoscope cover (briefly mentioned as a cover hereinafter) and an endoscope for an endoscope cover (briefly mentioned as a cover endoscope hereinafter) to be inserted into the endoscope cover.

Because the cover is abandoned after it is used, it is not required to have the same degree of durability as in the repeatedly used type endoscope. Thus, it may have a durability level sufficient for only one inspection and may be as inexpensive as possible.

Here, the cover most likely to be damaged is the cover part (mentioned as the inserted part cover part hereinafter) covering the inserted part to be inserted into the body of a patient.

A plurality of tube paths are provided within the inserted part cover part and are classified largely into the following two kinds.

One kind consists of thick walled tube paths such as endoscope inserting channels and fluid tube path housing channels. These tube paths are made of a comparatively soft bendable material. On the other hand, the other kind consists of thin walled tube paths such as air and water feeding and sucking tube paths within fluid tube path housing channels. These tube paths must have smooth surfaces for fluids to pass through them. A comparatively hard material is used to make them.

These tube paths are curved and bent with the curvature of the cover endoscope inserted through the endoscope inserting channels.

The problem in the case where the tube path is bent is that the radius of curvature of the part inside the bend will become so small that the tube path will buckle.

It is when the curvature angle of the cover endoscope is at a maximum that the radius of curvature inside the bend will become smallest. Particularly, the air and water feeding and sucking tube paths which are low in the durability to the bend and are hard and thin in the wall will be likely to buckle. Also, when the bending is repeated, the buckle will likely recur.

When these tube paths buckle, the wrinkles generated within the tube paths will tend to cause an obstruction of the flow of the fluid and the inspection will be interrupted.

In order to solve this problem, it is necessary to use a tube path material which will not buckle even at the time of the maximum curvature of the cover type endoscope.

However, with this method, the durability can be secured even in the direction in which the maximum curvature angle is not generated and it will be safe but with greater quality than necessary and it° will be difficult to provide the cover cheaply.

SUMMARY OF THE INVENTION

An object of the present invention is to provide an endoscope in an endoscope cover system wherein, even at the time of the maximum curvature or even when the curving is repeated, internal tube paths will not buckle.

Another object of the present invention is to provide an endoscope in an endoscope cover system which is low in cost and in which internal tube paths will not buckle.

In a formation wherein, at the time of the maximum curvature in the maximum curvature angle direction, in the direction intersecting substantially at right angles with the curvature direction, a rotation moment will act in a direction in which such fluid tube path as an air feeding tube path will move to the outside of the curvature. In case the fluid tube is curved near to the maximum curvature angle in the maximum curvature angle direction, the curved fluid tube path will be twisted so as to move to outside the curvature. By this mechanism of being curved and twisted, the fluid tube path desired to be prevented from buckling will have a larger radius of curvature than in the case in which the part inside the curvature is curved without being twisted and the fluid tube path will be able to be prevented from buckling.

BRIEF DESCRIPTION OF THE DRAWINGS

FIGS. 1 to 12 relate to the first embodiment of the present invention.

FIG. 1 is a general view showing the formation of an endoscope apparatus in a cover system provided with the first embodiment.

FIG. 2 is a sectioned view showing the formation of an endoscope in a cover system of the first embodiment.

FIG. 3 is a perspective view showing a tip part of an endoscope for a cover.

FIG. 4 is a perspective view showing a tip part of a cover.

FIG. 5 is a perspective view showing an endoscope of a cover.

FIG. 6 is a cross-sectional view taken along line A–A' in FIG. 4 showing an inserted part cover part.

FIG. 7 is a cross-sectional view showing a curving mechanism.

FIG. 8 is a cross-sectional view showing an operating part.

FIGS. 9a and 9b are explanatory views showing an endoscope of a cover system curved upward.

FIG. 10 is a perspective view showing a cover inserting part and an endoscope operating part fixing mouth body part as made a separable structure.

FIG. 11 is a cross-sectional view showing a connecting part of a cover inserting part and an endoscope operating part fixing mouth body part.

FIG. 15 is a perspective view showing a curving piece in the fourth embodiment.

FIG. 16 is a cross-sectional view showing a curving piece.

FIG. 17 is a cross-sectional view of an inserted part cover part in the position of a curving part as an inserted part is inserted through an endoscope inserting channel.

FIG. 19 is a general view showing the formation of an endoscope apparatus of a cover system provided with the sixth embodiment.

FIG. 20 is a cross-sectional view showing the formation of an endoscope of a cover system of the sixth embodiment.

FIG. 21 is a perspective view showing a tip part of an endoscope for a cover.

FIG. 22 is a perspective view showing a tip part of a cover.

FIG. 23 is a perspective view showing a tip part of an endoscope for a cover.

FIG. 24 is a cross-sectional view taken along line A–A' in FIG. 23.

FIG. 25 is a cross-sectional view showing a switch cover of an operating part cover part.

FIG. 26 is a cross-sectional view showing a UD knob removing mechanism taken along line B–B' in FIG. 23.

FIG. 27 is a side view of a UD knob switch as operated in FIG. 26.

FIG. 29 is a general view showing the formation of an endoscope apparatus of a cover system provided with the eighth embodiment.

FIG. 30 is a cross-sectional view showing the formation of an endoscope of a cover system of the eighth embodiment.

FIG. 31 is a perspective view showing a tip part of an endoscope for a cover.

FIG. 32 is a perspective view showing a tip part of a cover.

FIG. 33 is a perspective view showing a cover and a cover endoscope as separated.

FIG. 34 is a side view showing a hinge of an operating part cover part and a bridge cover as seen in the direction indicated by the arrow B in FIG. 33.

FIG. 35 is a cross-sectional view taken along line C–C' in FIG. 33.

FIG. 36 is a cross-sectional view showing the vicinity of an eyepiece cap.

FIG. 37 is a cross-sectional view showing the structure of the vicinity of an eyepiece part.

FIG. 38 is a view showing a cam hole for adjusting the visibility.

FIG. 39 is a cross-sectional view taken along line D–D' in FIG. 36.

DETAILED DESCRIPTION OF THE PREFERRED EMBODIMENTS

The embodiments of the present invention shall be explained in the following with reference to the drawings.

Figure 1:
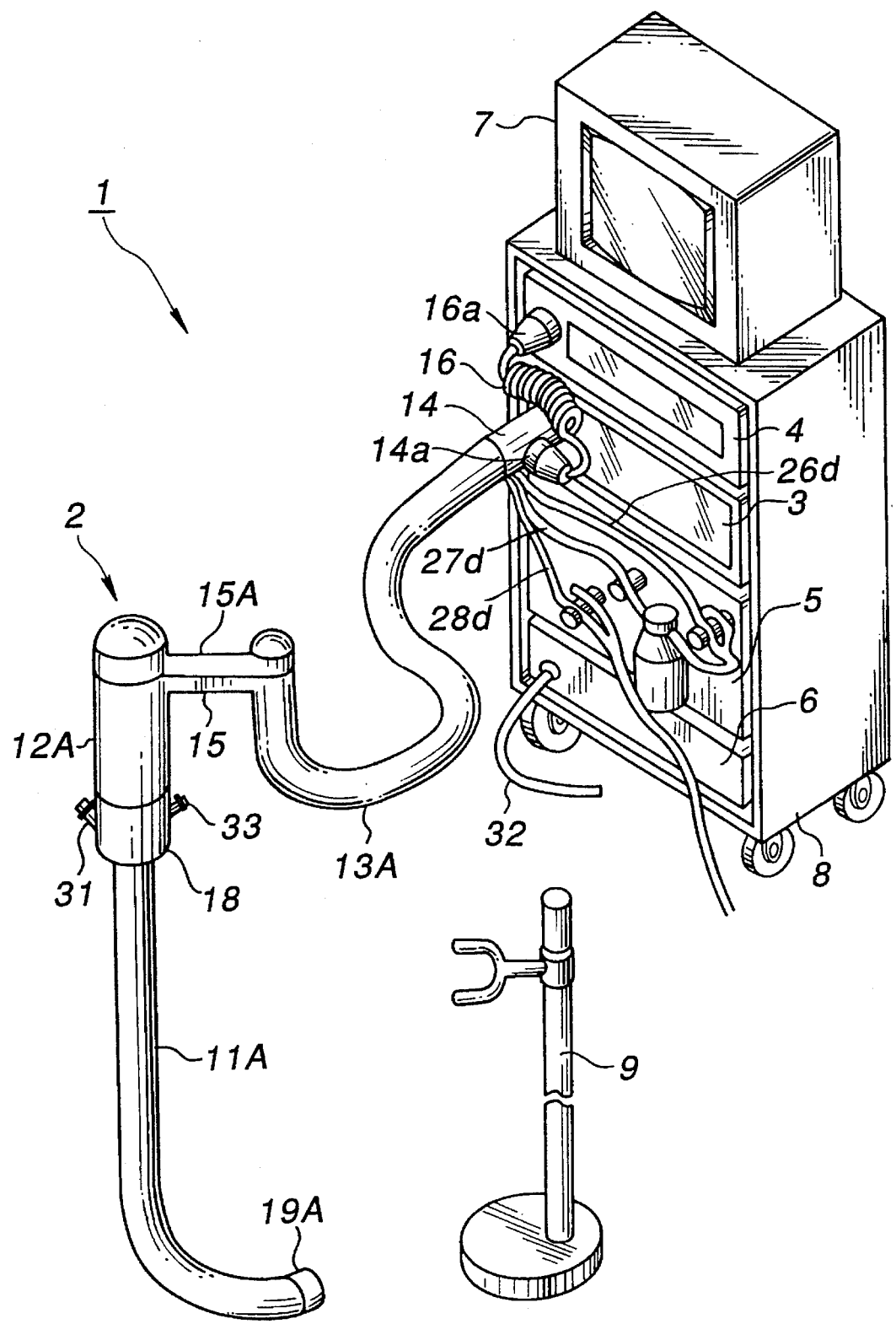

As shown in FIG. 1, an endoscope apparatus 1 in an endoscope cover system comprises an endoscope (which shall be briefly mentioned hereinafter as an endoscope in a cover system) 2 in an endoscope cover system fitted with a channel consisting of an endoscope cover (which shall be briefly mentioned hereinafter as a cover) 2A fitted with a channel of the first embodiment and a cover endoscope 2B fitted to this cover 2A, a light source apparatus 3 feeding this cover endoscope 2B with an illuminating light, a video processor 4 processing signals for an imaging means built-in in the cover endoscope 2B, a fluid controlling apparatus 5 feeding air and water through the tube of the cover 2A, an endoscope cover expander (which shall be briefly mentioned hereinafter as a cover expander) 6 fitted with a channel used to fit the cover endoscope 2B to the cover 2A and a monitor 7 displaying video signals processed by the above-mentioned video processor 4, the light source apparatus 3, video processor 4, fluid controlling apparatus 5 and cover expander 6 are housed in a cart 8 and the monitor 7 is mounted on the upper surface of the cart 8.

Figure 2:
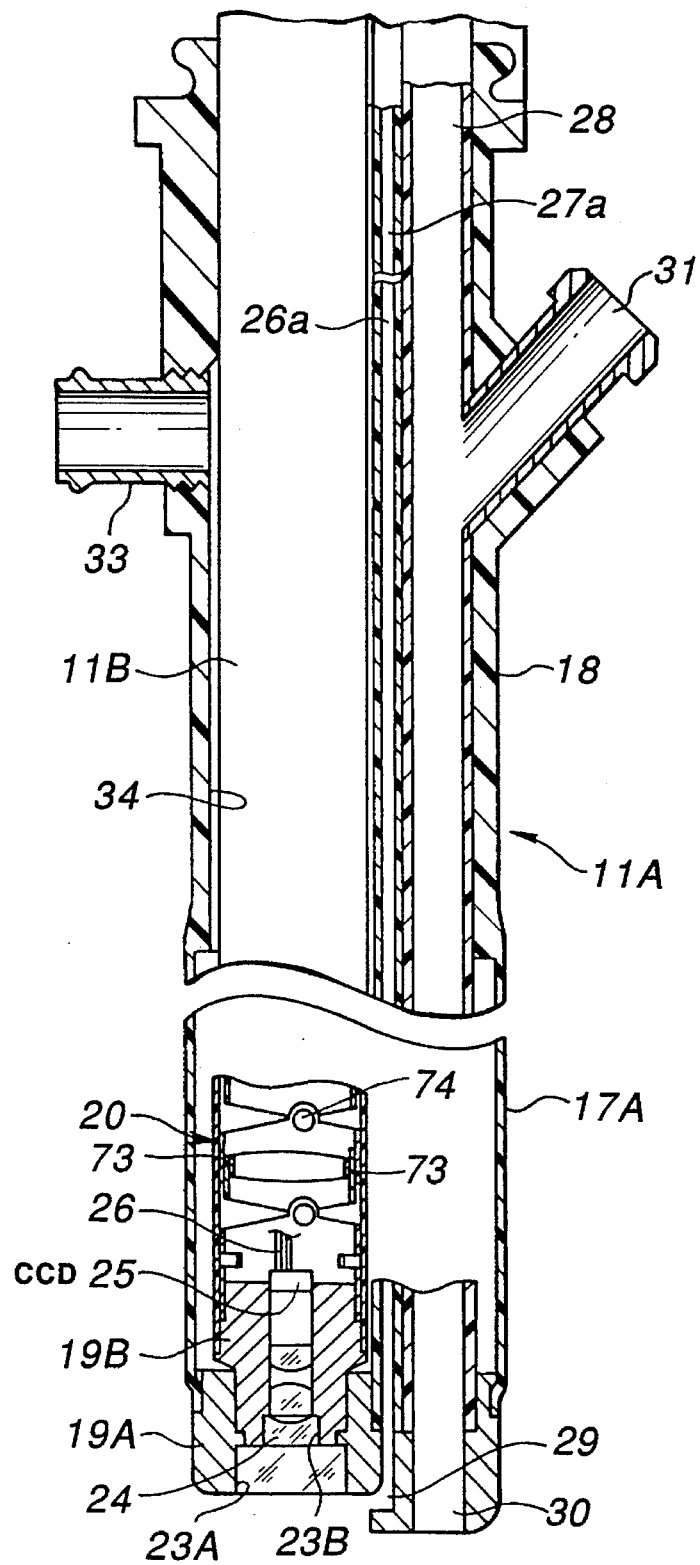

FIG. 2 shows a magnified view of the cover system endoscope 2 part in FIG. 1. In making an endoscope inspection, the clean cover endoscope 2B is covered with the clean cover 2A and, after the inspection, the cover 2A is abandoned. The cover endoscope 2B is then covered with the new clean cover 2A and is used repeatedly.

In fitting the cover endoscope 2B to an inserted part cover part 11A forming the cover 2A and in removing the fitted cover endoscope 2B, a cover holder 9 shown in FIG. 1 is used and, for example, with the cover 2A hung on the base end side on the cover holder 9, an endoscope inserted part 11B of the cover endoscope 2B is inserted or removed.

Figure 5:
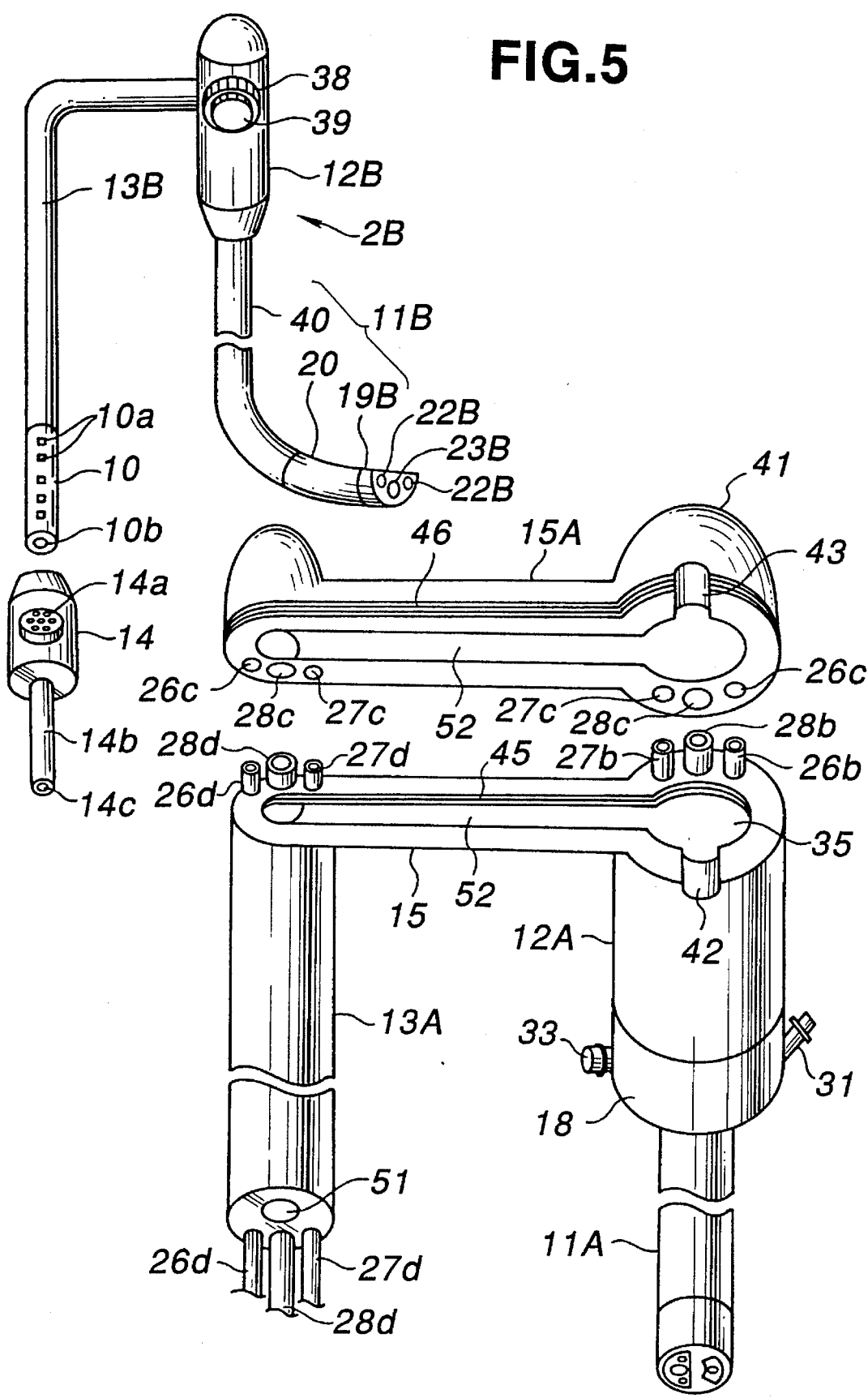

As shown in FIG. 5, the cover endoscope 2B comprises an elongate flexible endoscope inserted part (which shall be briefly mentioned hereinafter as an inserted part) 1ib of a semi-circular cross-section, an endoscope operating part (which shall be briefly mentioned hereinafter as an operating part) 12B formed on the proximal end side of this inserted part 11B and a universal cord extended out of the side of this operating part 12B. When a removable connector 14 is connected to a universal cord connector 10 at the end of this universal cord 13B so as to be removably connected to the light source apparatus 3, an illuminating light from a lamp within the light source apparatus 3 will be fed.

Electrical contacts 10a and an illuminating light incident end 10 are exposed on the above-mentioned universal cord connector 10 so that, when the connector adapter 14 is fitted, the electrical contacts 10a will conduct to electrical parts 14a of the connector adapter 14 and the illuminating light incident end 10b will be optically connected with an illuminating light incident end 14c of the connector 14 by a rod lens housed in a tube part 14b of the connector adapter 14.

As shown in FIG. 1, a signal connector 16a provided at the end of a signal cable 16 connected to the electrical contact parts 14a of the connector adapter 14 can be removably connected to the video processor 4.

Each of the above-mentioned inserted part 11B and universal cord 13B is covered with a flexible, air-tight and water-tight tube made of a synthetic resin, and the operating part 12B is also covered with a sheath member made of a synthetic resin so as to be both air-tight and water-tight.

The inserted part 11B comprises a tip part 19B, a curvable curving part 20 formed at the rear end of the tip part 19B and a long flexible part 40 formed at the rear end of the curving part 20. Rotation of a vertically curving knob (which shall be briefly mentioned hereinafter as a UD knob) 38 and a horizontally curving knob (which shall be briefly mentioned hereinafter as an RL knob) 39 causes the curving part 20 to be curved vertically and horizontally.

In the first embodiment, the cover endoscope 2B is an endoscope for lower digestion tracts, can be curved respectively by 180, 180, 160 and 160 degrees in four vertical and horizontal, that is, upward, downward, rightward and leftward (UD and RL) directions, and the maximum curvature angle directions are the U and D directions. The largest frequency of using the curvature is in the U direction. (The curvature in the U direction is used most frequently.)

On the other hand, the cover 2A comprises an inserted part cover part 11A and operating part cover part 12A, respectively covering the inserted part 11B and operating part 12B of the cover endoscope 2B, a universal cord cover part 13A covering the universal cord 13B, a bridge 15 connecting the operating part cover part 12A and universal cord cover part 13A and a bridge cover 15A for closing the opening of this bridge 15.

As shown in FIG. 2, the inserted part cover part 11A comprises an inserted part cover outer cover 17A covering the inserted part 11B, an endoscope operating part fixing mouth body part 18 provided air-tightly and water-tightly at the proximal end of this inserted part cover outer cover 17A and a cover tip part 19A provided air-tightly and water-tightly at the distal end of the inserted part cover outer cover 17A.

The illuminating light incident upon the illuminating light incident end 14c of the connector adapter 14 from a lamp, not illustrated, within the above-mentioned light source apparatus 3 is transmitted by a light guide formed of optical fiber bundles, not illustrated, and is projected though an end surface fixed to the tip part 19B of the inserted part 11B and illumination optical system fitted to illuminating windows 22B (see FIG. 3) opposed to this end surface.

Figure 3:
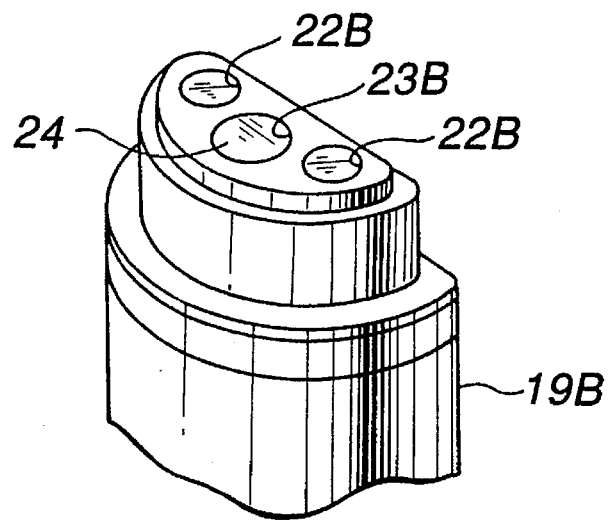

As shown in FIG. 3, the illuminating windows 22B and an observing window 23B are arranged adjacent to one another on the tip part 19B of a semi-circular cross-section. The illuminating light projected through the illuminating light optical systems of these illuminating windows 22B is projected to the object side in front through transparent plates of cover illuminating windows 22A (see FIG. 4) which cover the tip part 19B.

The illuminated object forms an optical image in the focal plane of an objective optical system 24 through a transparent plate of a cover observing window 23A provided adjacently to the cover illuminating windows 22A and the objective optical system 24 (see FIG. 2) fitted to the observing window 23B provided opposite and inside the observing window 23A.

The tip of the soft inserted part cover outer cover 17B for isolating the inserted part 11B of the cover endoscope 2B from the external environment is air-tightly and water-tightly connected to a cover tip part 19A provided with the cover illuminating windows 22A and cover observing window 23A.

A CCD 25 is arranged in the focal plane of the objective optical system 24. An optical image is photoelectrically converted, is input into the video processor 4 through the signal cable inserted through the inserted part 11B and universal cord 13B and the signal cable 16 connected to the connector adapter 14 and is processed as a signal. Then, a standard video signal is produced and is input into the monitor 7 and an object image is displayed on the displaying picture.

Figure 4:
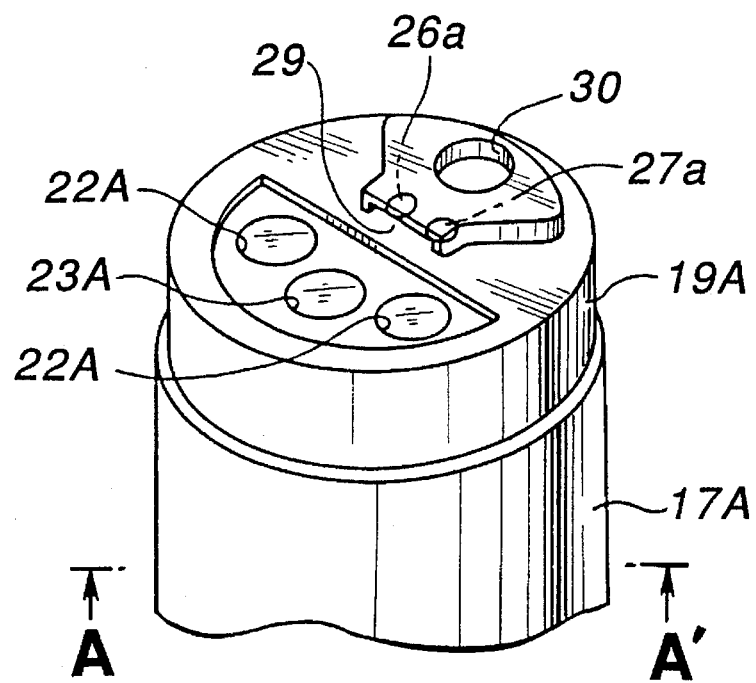

Within the inserted part cover part 11A, the air feeding tube, water feeding tube and sucking tube shown in FIG. 2 are provided to form, respectively, an air feeding tube path 26a, water feeding tube path 27a and sucking tube path 28a. As shown in FIG. 4, the tips of the air feeding tube path 26a and water feeding tube path 27a communicate with a nozzle 29 of the cover tip part 19A and the tip opening of this nozzle 29 is opposed to the outer surface of the cover observing window 23A.

The proximal end sides of the air feeding tube path 26a and water feeding tube path 27a are extended out upward of the endoscope operating part fixing mouth body part 18 together with the sucking tube path 28a, are inserted though the bridge cover 15A and universal cord 13B, as described later, are then extended out of the tip of the universal cord 13B and are connected to the fluid controlling apparatus 5. Therefore, body liquid deposited on the observing window 23A may be removed by feeding air or water through the air feeding tube path 26a or water feeding tube path 27a.

A forceps inserting port 31 and an expanding tube mouth body 33 connecting an expanding tube 32 connected to the cover expander 6 are provided on the side surface of the above-mentioned endoscope operating part fixing mouth body part 18. As shown in FIG. 2, the forceps inserting port 31 joins with the sucking tube path 28a and opens at the forceps outlet 30 which has also a function of a sucking port in the cover tip part 19A.

As shown in FIGS. 2 and 5, an opening part 35 of an endoscope inserting channel 34 for inserting (fitting) the inserted part 11B of the cover endoscope 2B is provided on the upper surface of the endoscope operating part fixing mouth body part 18.

This opening part 35 communicates with the expanding tube mouth body 33 provided to open on the side of the endoscope operating part fixing mouth body part 18.

This endoscope inserting channel 34 opens out through the opening part 35 which is formed on the proximal end side and though which the inserted part 11B is inserted and the expanding tube mouth body 33 to which the expanding tube 32 is connected but the channel 34 is not otherwise exposed to the outside. Therefore, in case the inserted part 11B is inserted, this inserted part 11B will be covered but its proximal end side with a channel forming member (such as the inserted part cover outer cover 17A) forming the endoscope inserting channel 34 is not exposed to the outside. The operating part 12B on the proximal end side of the inserted part 11B will be also covered with the operating part cover 12A and an operating part cap 41 of a bridge cover 15A shown in FIG. 5.

As shown in FIG. 5, the operating part cover part 12A is provided with a U-shaped groove 42 in the position corresponding to the rotary shaft of the UD knob 38 and RL knob 39 of the operating part 12B and the operating part cap 41 is also provided with a U-shaped groove 43 in the position corresponding to the rotary shaft.

The opening end part 26b of the air feeding tube path 26a, the opening end part 27b of the water feeding tube path 27a and the opening end part 28b of the sucking tube path 28a are projected on the periphery of the opening part 35.

A recess 45 is provided on the inside surfaces of the operating part cover part 12A and bridge 15. On the other hand, a projection 46 is provided on the outer periphery of the bridge cover 15A and is combined with the above-mentioned recess 45. The operating part cover part 12A and bridge 15 and the bridge cover 15A open in the plane passing through the rotary shaft of the UD knob 38 and RL knob 39 and can be separated into two bodies.

The bridge cover 15A is provided at both ends with air feeding tube paths 26c, water feeding tube paths 27c and sucking tube paths 28c exposing respective opening ends. The opening ends on one side are connected respectively to the opening end part 26b of the above-mentioned air feeding tube path 26a, the opening end part 27b of the water feeding tube path 27a and the opening end part 28b of the sucking tube path 28a of the operating part cover part 12A. The opening ends on the other side are connected respectively to the respective opening ends on the bridge side of the air feeding tube path 26d, water feeding tube path 27d and sucking tube path 28d of the universal cord cover part 13A.

The air feeding tube path 26d, water feeding tube path 27d and sucking tube path 28d extended out of the tip of the universal cord cover part 13A are connected to the fluid controlling apparatus 5 shown in FIG. 1.

A universal cord inserting tube path 51 of a diameter larger than the outside diameter of the universal cord 13B is provided within the universal cord 13A. A groove part 52 which can house the universal cord 13B is also provided in the bridge 15 and the bridge cover 15A.

Figure 6:
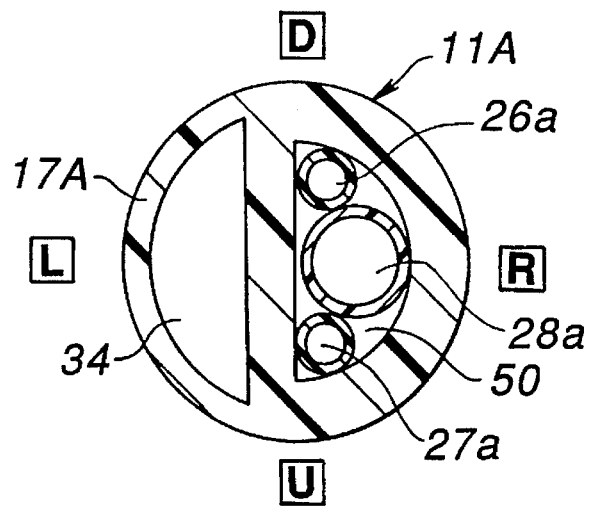

FIG. 6 is a cross-sectional view (along line A–A' in FIG. 4) of the inserted part cover part 11B. In FIG. 6, the vertical and horizontal directions respectively correspond to the DU and RL directions.

An endoscope inserting channel 34 of a semi-circular cross-section is provided on the L side within the inserted part cover part 11B and a fluid tube path housing channel 50 of a semi-circular cross-section is provided on the R side in the same manner. The fluid tube path housing channel 50 is not arranged on the U side where the using frequency is the highest. Also, the fluid tube path housing channel 50 is arranged on the side where the direction (U or D direction) in which the maximum curvature angle is generated is avoided.

This endoscope inserting channel 34 is connected so that air from the expanding tube mouth body 33 may flow in.

The above-mentioned air feeding tube path 26a, water feeding tube path 27a and sucking tube path 28a are provided within the fluid tube path housing channel 50.

Here, these tube paths through which a fluid flows are made of material having a smooth surface, such as, for example, polytetrafluoroethylene. Though having a smooth surface, such material is so weak in bending that, when a strong bending force is applied, the inside radius of curvature will become so small that the material will buckle.

On the other hand, the inserted part cover outer cover 17A of the inserted part cover part 11B need not have as smooth a surface and is therefore made of such soft material exhibiting good bending characteristics as, for example, urethane rubber, silicone rubber or elongated polytetrafluoroethylene. The inserted part cover outer cover 17A is made relatively thin from the endoscope inserting channel 34 to the outer periphery, and is relatively thick elsewhere.

The inserted part cover outer cover 17A is formed to have high flexibility in the L direction side but to have low flexibility in the R direction side where the fluid tube path housing channel 50 is located. In other words, whenever a curving force acts, the L direction side will tend to curve easily while the R side tends to resist curvature. Therefore, it can be said that the resistance to curvature is higher on the R direction side than on the L direction side.

By the way, in this embodiment, the fluid tube path housing channel 50 is arranged on the R side but may be arranged in the D and L directions where the using frequency is low.

In such case, the outer cover 19 is formed to be relatively thin from the endoscope inserting channel 34 to the outer periphery but to be relatively thick otherwise.

The curving mechanism operated by the UD knob 38 and RL knob 39 provided in the operating part 12B shall be explained with reference to FIG. 7.

Figure 7:
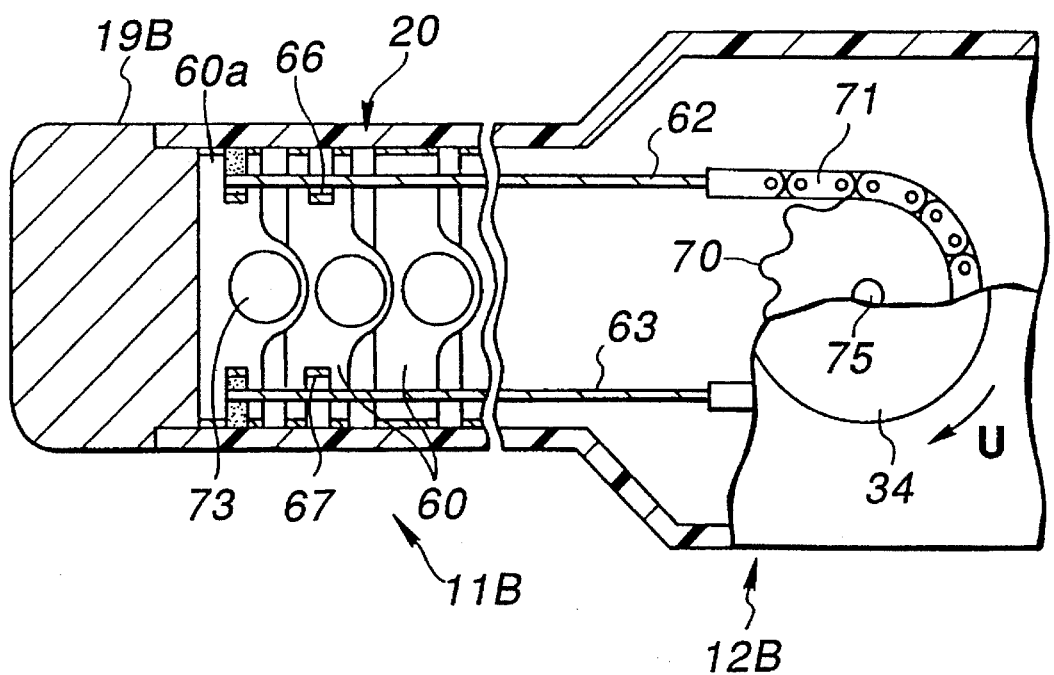
Figure 8:
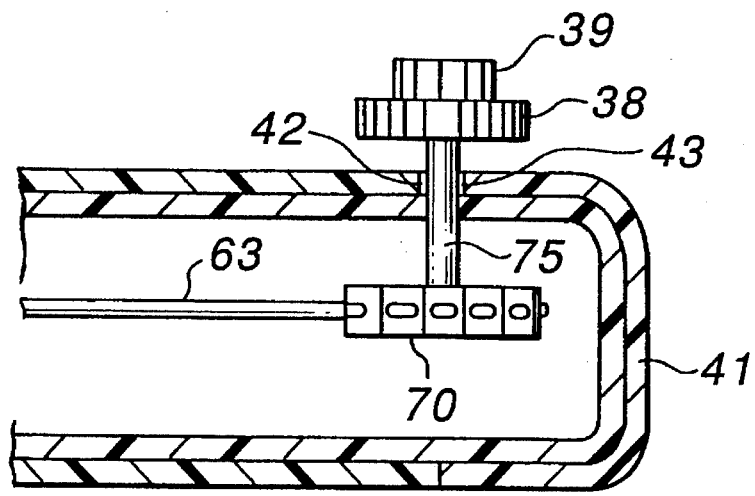

As shown in FIG. 7, the UD knob 38 is connected with a sprocket 70 within the operating part 12B by a rotary shaft 75. By the way, in FIGS. 7 and 8, for brevity, only the curving mechanism on the UD sides is shown. A chain 71 is wound on the sprocket 70 and is connected at the ends, respectively, with a U side wire 62 and D side wire 63.

The wires 62 and 63 are supported by a U side wire receiver 66 and D side wire receiver 67 provided on a curving piece 60 within the inserted part 11B and are then connected to a curving piece 60a. By the way, the adjacent curving pieces 60a and 60 are rotatably connected in the UD directions by a pair of rivets 73 (in FIG. 7, a pair of rivets 73 opposed to each other in the direction vertical to the paper surface on only one side are shown) provided in the positions opposed to each other.

In this formation, when the knob 38 is rotated in the U direction, the sprocket 70 will rotate clockwise, the curving piece 60a at the tip of the inserted part 11B will be pulled through the chain 71 and U side wire 62 and thereby the curving part 20 on the tip side of the inserted part 11B will be curved in the U direction with the rivets 73 which are pivotally supporting members as a rotation center.

To explain with reference to FIG. 2, the pair of opposed rivets 73 connect the adjacent curving pieces 60 so as to be rotatable in the UD directions and a pair of opposed rivets 74 (in FIG. 2, only one side is shown) intersecting substantially at right angles with the pair of rivets 73 connect the adjacent curving pieces 60 so as to be rotatable in the RL directions.

It is a main feature of the present invention to include a twisting curving mechanism wherein, in this embodiment, in case a tension for curving acts, the curving part will be relatively easy to rotate (curve) on the endoscope inserting channel 34 side but resistant to rotation on the fluid tube path housing channel side on the other side around the axis connecting the pair of opposed rivets 74 and, in case the curving part is curved near to the maximum curvature angle in the U direction in which the maximum curvature angle is set, the curving part will be twisted so that the endoscope inserting channel 34 side, which is relatively easy to curve, will be inside the curvature, but the fluid tube path housing channel side more difficult to curve will be outside the curvature.

Figure 10:
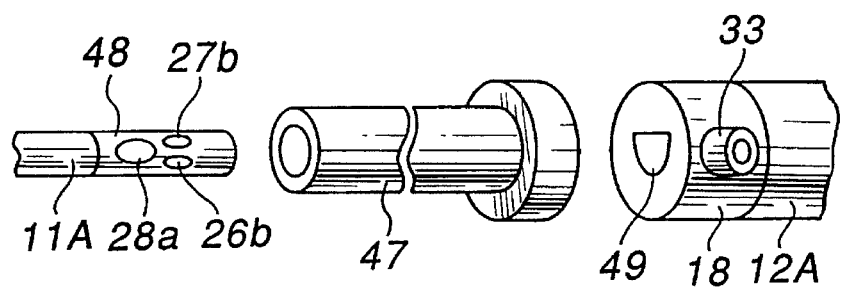

By the way, as a modification of the first embodiment, as shown in FIG. 10, the endoscope operating part fixing mouth body part 18 and the inserted part cover part 11B may be made separable from each other and the outside diameter of the proximal end part of the inserted part cover part 11B as separated may be set to be smaller than the inside diameter of the sliding tube 47.

With such structure, for example, the sliding tube 47 can be inserted from the endoscope operating part fixing mouth body part 18 side of the inserted part cover part 11B. Also, in this structure, the inserted part cover connector 48 is fixed to the proximal end part of the inserted part cover part 11B.

The air feeding tube path 26a, water feeding tube path 27a and sucking tube path 28a all open on the outer periphery of this inserted part cover connector 48.

Also, the inserted part cover connector 48 has a D-shaped cross-section, not illustrated, and can be inserted into a D-shaped hole 49 of the endoscope operating part fixing mouth body part 18 of the operating part cover 12A.

Figure 11:
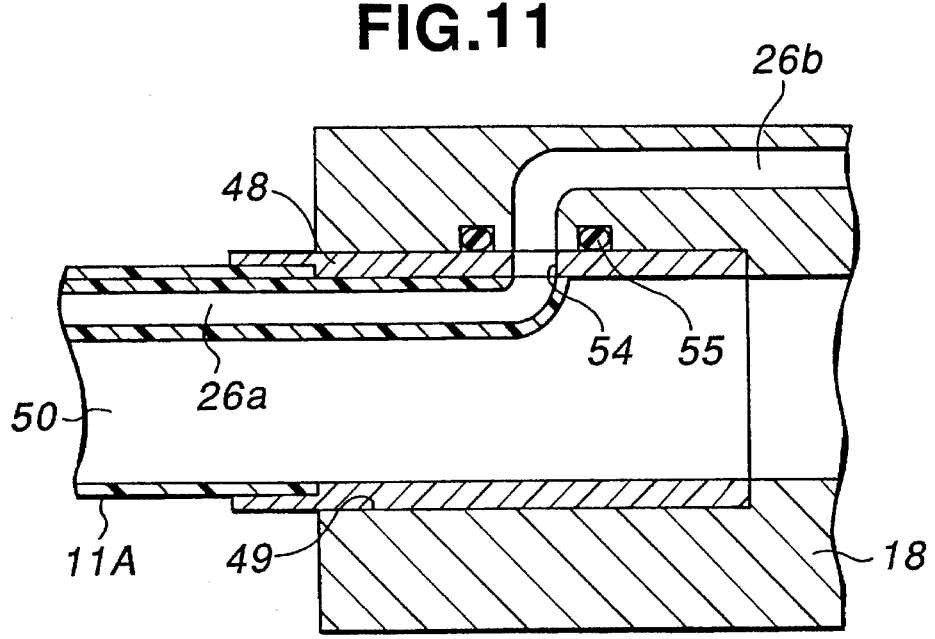

FIG. 11 shows a cross-sectional view of the inserted part cover connector 48 as inserted in the D-shaped hole 49.

The air feeding tube path 26a provided within the inserted part cover part 11B is bonded and fixed at the opening end to the hole 54 provided in the inserted part cover connector.

When fitted within the D-shaped hole 49, this hole 54 will communicate with the opening end of the air feeding tube path 26b provided in the endoscope operating part fixing mouth body part 18. On the periphery of the opening end of this air feeding tube path 26b, a ring-like recess is provided to surround the opening end and an O-ring 55 is housed in the ring-like recess so that the air feeding tube paths 26a and 26b may be prevented by the O-ring 55 from leaking the fluid.

The water feeding tube path and sucking tube path are of the same structure and shall be omitted. The O-ring may be separately provided for each tube path or may be integrally molded.

The procedures from the fitting to inspection of the cover 2A in this first embodiment (and modification) shall be explained in the following.

In FIG. 1, the cover holder 9 is covered with a cover holder cover (not illustrated) and then the endoscope fixing mouth body part 18 of the cover 2A is set.

The cover expander 6 is switched on. Thereby, air is fed from the open end of the expanding tube 32. The expanding tube 32 is fitted to the expanding tube mouth body 33 of the cover 2A.

Thereby, air is fed into the endoscope inserting channel 34 in FIG. 6 and the endoscope inserting channel 34 expands.

Here, the inserted part 11B of the cover endoscope 2B is inserted into the endoscope inserting channel 34. The expansion of the endoscope inserting channel 34 allows smooth insertion of the inserted part 11B.

As shown in FIG. 2, the tip part 19B of the inserted part 11B is set at the tip of the inserted part cover part 11A and the operating part 12B is also set in the operating part cover part 12A. At this time, the rotary shaft, not illustrated, of the UD knob 38 and RL knob 39 in FIG. 5 will be positioned in the U-shaped groove 42. The expanding tube 32 is removed.

Then, the universal cord 13B is inserted into the universal cord inserting tube path 51 of the universal cord cover part 13A.

Because the universal cord inserting tube path 51 is larger than the universal cord 13B, the universal cord 13B can be smoothly inserted.

At this time, the universal cord connector 10 of the universal cord 13B will project out-of the tip of the universal cord cover part 13A.

Here, the connector adapter. 14 is fitted to the universal cord connector 10.

Then, the illuminating light incident end 14c and the illuminating light incident end 10b of the cover endoscope 2B will be optically connected and the illuminating light incident end 14c and the illuminating optical system 22B provided in the tip part 19B of the inserted part 11B of the cover endoscope 2B will be optically connected.

Also, the electrical contact 10a of the cover endoscope 2B will be electrically connected to the electric contact part 14a of the adapter 14.

Here, when the tube part 14b is connected to the light source apparatus 3 in FIG. 1, the illuminating light will be led to the illuminating optical system 22B.

When the connector 16a is connected with the video processor 4 through the cable 16 in FIG. 1, the image from the objective optical system 24 in FIG. 5 will be converted to an electrical signal and the electrical signal will be led to the video processor 4 in FIG. 1 and will be converted here to a video which will be displayed in the monitor 7.

Here, the bridge cover 15A is pressed against the side of the operating part cover 12a and bridge 15.

Then, the projection 46 on the outer periphery of the bridge cover 15A and the recess 45 on the inside surface of the operating part cover part 12A and bridge 15 will be engaged and connected with each other. They are shown as connected in FIG. 8.

Due to the U-shaped grooves 42 and 43, the rotary shaft 74 will not interfere with the cover 2A. As shown in FIG. 5, the air feeding tube path 26d, water feeding tube path 27d and sucking tube path 28d projected out of the universal cord cover part 13A are connected to the fluid controlling apparatus 5 in FIG. 1.

Here, the endoscope inspection is ready to be made and the inserted part cover part 11B is inserted into the body of the patient.

In case a sliding tube 47 is to be used, the endoscope inserting channel 34 is expanded with the cover expander 6, the cover endoscope 2B is pulled out of the cover 2A and then the inserted part cover part 11B is separated from the operating part cover part 12A. Here, the sliding tube 47 is inserted from the end part of the inserted part cover part 11B (see FIG. 10).

After the insertion, the inserted part cover part 11B and the operating part cover part 12A are connected with each other and then the cover endoscope 2B is set to the cover 2A so that the sliding tube 47 may be fitted without pulling the inserted part cover part 11A out of the body of the patient.

As shown in FIG. 7, when the inserted part cover part 11B is to be curved in the U (upper) direction, the UD knob 38 is rotated in the direction corresponding to the U direction.

Then, the sprocket 70 within the operating part 12B will also rotate and the curving piece 72 on the tip side of the inserted part 11B of the cover endoscope 2B within the inserted part cover part 11A will be pulled through the chain 71 wound on the sprocket 70 and the U side wire 62.

Then, the curving part 20 on the tip side of the inserted part 11B will curve substantially in the U direction.

Here, the inserted part cover part 11A is on the periphery of the inserted part 11B as in the cross-sectional view shown in FIG. 6 and the inserted part 11B is within the endoscope inserting channel 34.

Here, if the cover endoscope 2B curves in the U direction, the inserted part cover part 11B will also curve in the U direction but, at this time, the inserted part cover part 11A will be a resistance body which obstructs the curving. The larger the curvature angle, the larger the influence of the inserted part cover part 11A as a resistance body.

Now, the inserted part cover part 11A is set to be larger in the rigidity on the rivet axis (the axis vertical to the paper surface and passing through the rivet 74, the later described line passing through the centers of the rivet holes 61 in FIG. 16 or the axis passing through the rivets 74 in FIG. 17) for horizontally curving the cover endoscope 2B on the tube path side (R side), and it will act as a resistance body larger than on the channel 34 (L) side.

Figure 9:
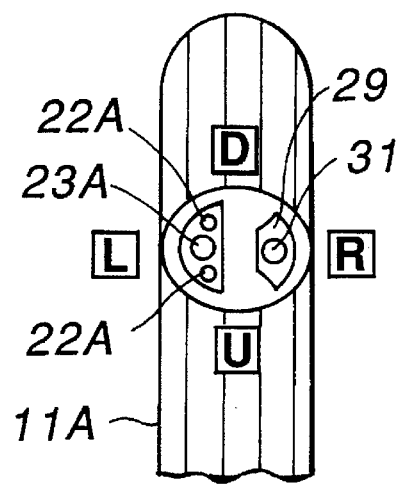
Figure 9:
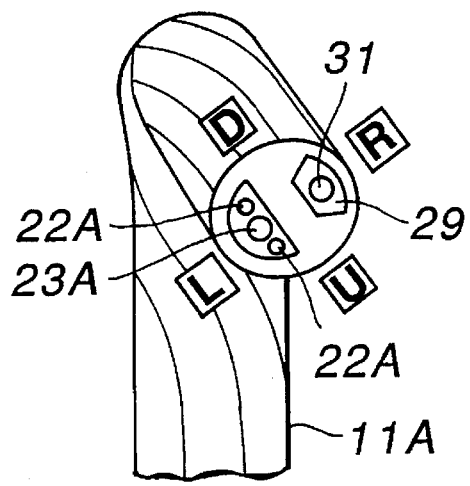

On the other hand, the channel 34 (L) side is set to be easy to curve. Therefore, if a large curvature is applied, the L side which is easy to curve will curve more than the R side (the R side is less in the curvature than the L side) and therefore the tube path side (R side) will be twisted on the outside (D side reverse to the curving direction) of the curvature of a large radius of curvature and will curve, as shown in FIG. 9b.

In FIGS. 9a and 9b, a plurality of lines in the axial direction of the inserted part cover part 11A are drawn on the outer surface of the inserted part cover part 11A to show how the inserted part cover part 11A is twisted and curved in this embodiment.

As understood from the lines in FIG. 9b, in case the curving part is operated to be curved near to the maximum curvature angle in the U direction, as the L side (the endoscope inserting channel side through which the cover endoscope 2B is inserted) of the cover inserting part 11A is structured to be easier to curve than the R side, the curving part will be curved as twisted so that the L side may be the inside (that is, the side of a small radius of curvature) and the R side may be the outside (that is, the side of a large radius of curvature).

That is to say, the fluid tube path side will be curved and moved to the outside of the curvature where the radius of curvature will be large. In case the curvature angle of the entire inserted part is constant, the radius of curvature will be larger than in case the tube path does not move (FIG. 9a) and the buckling will be harder to cause.

Figure 12A:
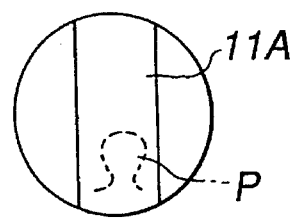
FIGS. 12a and 12b are explanatory views showing a visual field in the case of FIGS. 9a and 9b.
Figure 12B:
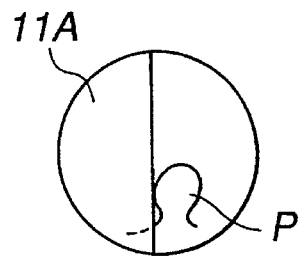

In case twisting is not generated at the time of curving, if nearly 180 degrees of curving is applied, the inserted part cover part 11A will appear in the middle of the visual field and the visual field will be obstructed, as shown in FIG. 12a. However, when the curving part is twisted as in this embodiment, as shown in FIG. 12b, the inserted part cover part 11A will lag to the periphery of the visual field and a polyp behind it will become easy to observe.

Further, according to this embodiment, even if the curving part is curved to the maximum curvature angle, it will be curved as twisted and therefore even a thin cover will be able to be prevented from buckling, thereby reducing cost. Also, the outside diameter of the inserted part inserted into the patient can be made small and the pain inflicted upon the patient can be reduced.

FIG. 9b shows the curving part as curved near to the maximum curvature angle in the U direction. However, even in case it is curved near to the maximum curvature angle in the D direction, in the same manner, the side through which the fluid tube path is inserted will be curved and twisted so as to move to the side on which the radius of curvature will become larger.

According to this first embodiment, in case the cover endoscope 2B is operated to be curved to the maximum curvature angle, such fluid tube path as the air feeding tube path 26a will act to escape in the direction in which the radius of curvature will become larger from the inside of the curvature, the inserted part cover part 11A will be curved and twisted and therefore the air feeding tube path 26 will be more difficult to buckle.

Further, even if the curving part 20 is curved largely, the tip side will be curved so as to be twisted, therefore the inserted part cover part 11A intercepting the observing visual field will move to either the right or left of center of the visual field and the observing visual field will be always secured.

The second embodiment shall be explained below. The cover endoscope 2B which is for lower digestion tubes in the first embodiment is made for upper digestion tubes in this second embodiment in which the inserted part cover part 11A is formed by fusing two elastic bodies having different respective degrees of hardness.

Figure 13:
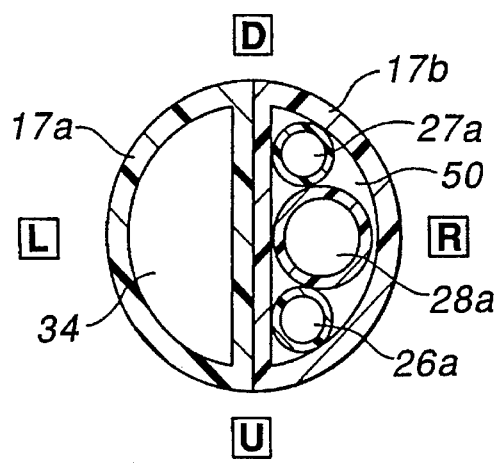
FIG. 13 is a cross-sectional view showing an inserted part cover part in the second embodiment of the present invention.

FIG. 13 is a cross-sectional view of the inserted part cover part 11A in the second embodiment.

In the drawing, the letters D, U, R and L correspond respectively to the up, down, right and left directions.

The cover endoscope in the second embodiment has the same shape and formation as the first embodiment, not illustrated, and has curvature angles of 210, 90, 100 and 100 degrees, respectively, in the U, D, R and L directions and can be curved to the maximum curvature angle in the U direction. Also, as in the first embodiment, the curvature in the U direction has the highest curving frequency of use.

The rest of the first embodiment has the same formation as the first embodiment and therefore the same components shall bear the same reference numerals and shall not be explained here.

In FIG. 13, the reference numeral 17a represents an outer cover (of the inserted part cover) made of a soft elastic material and contains an endoscope inserting channel 34.

The reference numeral 17b represents an outer cover made of a hard elastic material and contains a fluid tube path housing channel 50.

As in the first embodiment, the air feeding tube path 26a, water feeding tube path 27a and sucking tube path 28a are provided within the fluid tube path housing channel 50.

Here, the outer covers 17a and 17b are connected with each other by fusing to form the inserted part cover part 11A. The other elements are the same as in the first embodiment and therefore shall not be explained here.

The operation shall be explained below.

When the cover type endoscope is put into the endoscope inserting channel 34 and is curved in the U direction, the inserted part cover part 11A will be also curved in the U direction but, as the curvature angle becomes larger, the U side inserted part cover part 11A will become more difficult to compress and will be twisted so that the soft outer cover 17a may be inside and the hard outer cover 17b may be outside.

When thus curved, the tube paths will escape in the L direction and therefore the inside radii of curvature of the fluid tube path housing channel 50 and the air feeding, water feeding and sucking tube paths within it will become larger than when they are curved simply in the U direction. The effects of this embodiment are the same as of the first embodiment.

The third embodiment shall be explained below. In the first embodiment, the air feeding, water feeding and sucking tube paths are formed, respectively, of tubes but, in the third embodiment, instead of them, the inserted part cover part 11B is made a multilumen tube.

Figure 14:
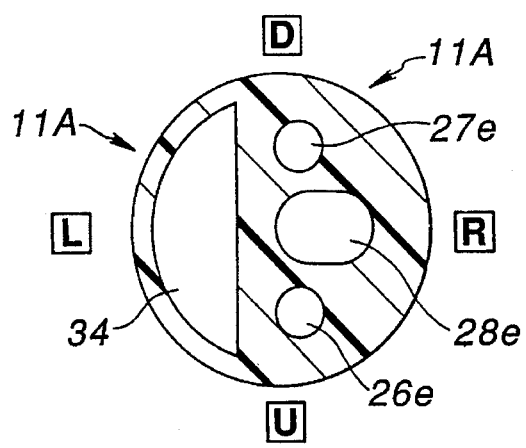
FIG. 14 is a cross-sectional view showing an inserted part cover part in the third embodiment of the present invention.

FIG. 14 is a cross-sectional view of the inserted part cover part 11A of the third embodiment.

In FIG. 14, the U, D, R and L respectively correspond to the up, down, right and left directions.

The endoscope inserting channel 34 of a semi-circular cross-section is provided on the L side within the inserted part cover part 11A and the air feeding channel 26e, water feeding channel 27e and sucking channel 28e are provided on the R side.

These channels are respectively connected with the air feeding tube path B26b, water feeding tube path B27b and sucking tube path B28b (not illustrated) as in the first embodiment.

The other structures are the same as in the first embodiment, therefore the same components shall bear the same reference numerals and shall not be explained here.

The operations and effects of this embodiment are the same as in the first embodiment.

The fourth embodiment shall be explained below. In this fourth embodiment, in case a curving operation is made in the U direction, the cover endoscope itself will fall in the L direction (that is, in the reverse direction on the R side of the fluid tube path).

Figure 15:
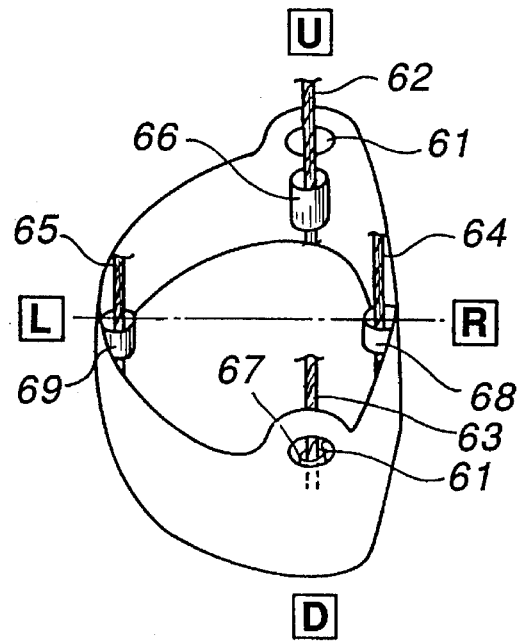
FIGS. 15 to 17 relate to the fourth embodiment of the present invention.

FIG. 15 shows a D-shaped curving piece within the cover endoscope inserting part. FIG. 16 is a cross-sectional view through rivet holes 61. In FIGS. 15 and 16, the U, D, R and L correspond respectively to the up, down, right and left directions. In the drawings, the proximal (up) side corresponds to the operating part side and the down side corresponds to the inserted part tip side (as seen in the direction reverse to that in FIGS. 4 and 9).

As in the first embodiment, this cover endoscope has a highest using frequency in the U direction. When the inserted part of this cover endoscope is fitted to the cover, as shown in FIG. 17, such fluid tube path as the air feeding tube path 26a will be housed within the fluid tube housing channel 50 on the right side of the R wire receiver 68.

Figure 17:
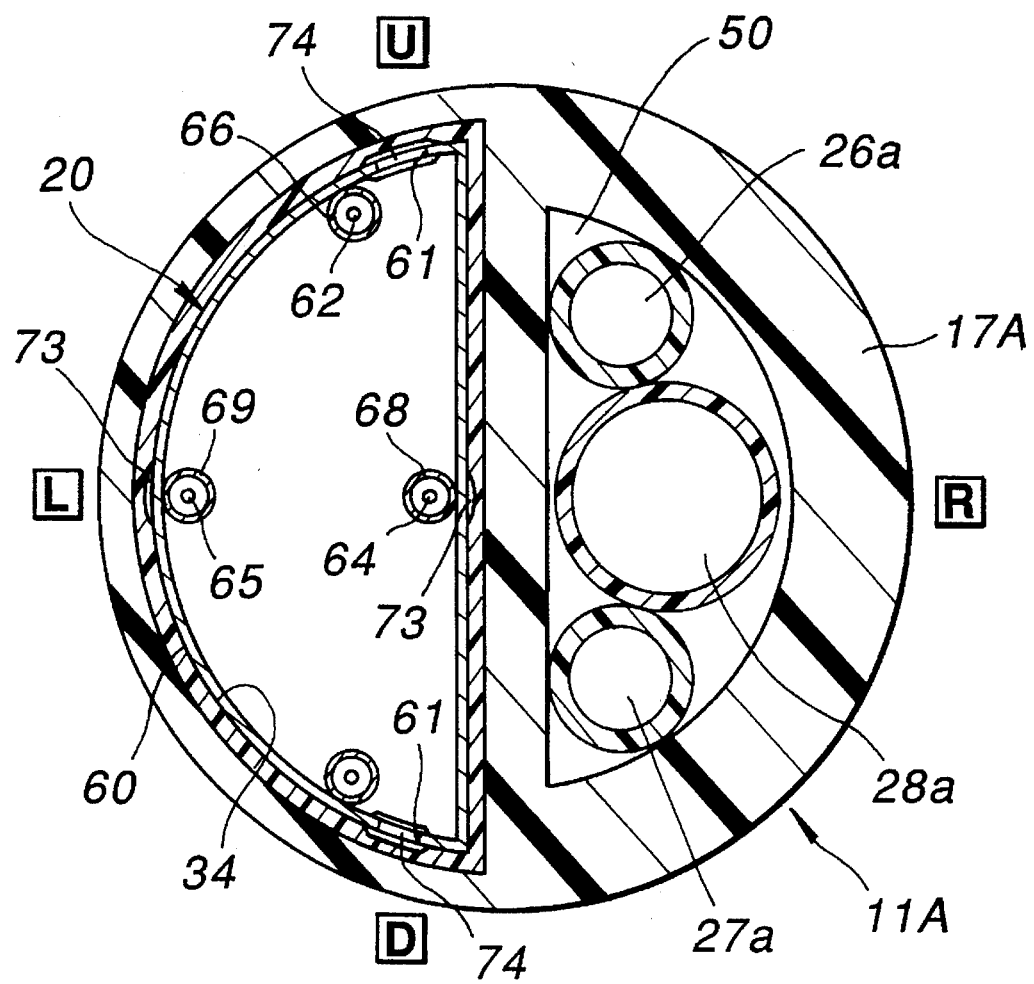

A pair of rivet holes 61 provided in opposed positions in the curving piece 60 are superimposed on a pair of rivet holes in the adjacent curving piece so as to communicate with them and rivets 73 and 74 shown in FIG. 17 are respectively inserted into the rivet holes to rotatably connect the curving pieces.

In FIG. 15, only the RL curving rivet holes 61 on the upper side of the curving piece 60 are seen but, on the opposite side of the curving piece, that is, on the down side in the drawing, UD curving rivet holes 61 are also provided and the respective curving pieces are connected rotatable in the U, D, R and L directions.

In FIG. 17, around the axis passing through the rivets 74, the curving piece 60 is curvably pivoted (rotatably) in the RL directions and, around the axis passing through the rivets 73, the curving piece 60 is rotatably connected in the UD directions.

A U side curving wire 62, D side curving wire 63, R side curving wire 64 and L side curving wire 65 and a U side wire receiver 66, D side wire receiver 67, R side wire receiver 68 and L side wire receiver 69 determining the supporting positions of these wires are provided within the curving piece 60. The respective tips of the wires 62, 63, 64 and 65 are fixed in the foremost curving piece or tip part.

In FIG. 17, when an operation of pulling, for example, the U side curving wire 62 is made, around the axis passing through the rivets 74, the U side of the curving piece 60 will be pulled toward the operating part side and the curving part 20 will be curved toward the U side. The curving in other directions is similar.

Figure 16:
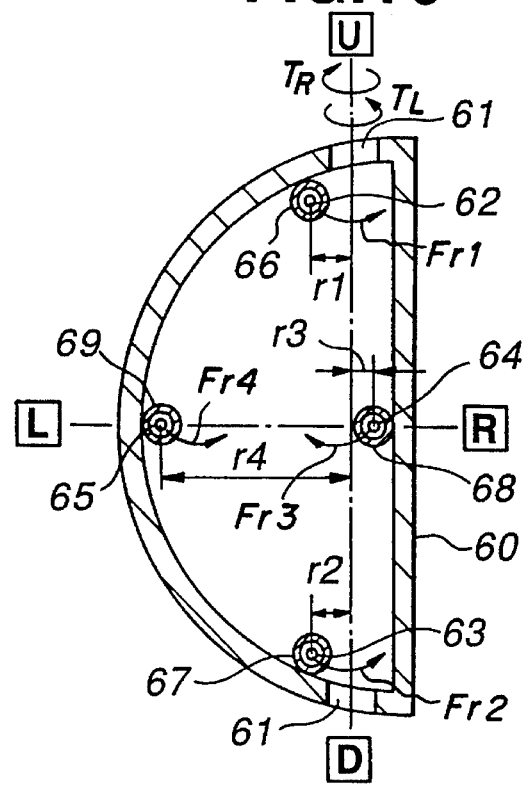

In FIG. 16, the above mentioned U, D, R and L side wire receivers are separated respectively by the distances r1, r2, r3 and r4 from the axis connecting the rivet holes 61.

Here, the U, D, R and L side curving wires are adjusted in length so that tensions may be applied downward in FIG. 16, respectively, at F1, F2, F3 and F4 in the natural state and are fixed.

Thereby, the peripheral U, D, R and L side wire receivers will be also subjected respectively to the forces of F1, F2, F3 and F4 in the proximal direction in FIG. 16.

Here, the relations of the tensions shall be $F1=F2=F3=F4=F$ and the relations of the distances shall be $r3<r1+r2+r4$.

Here, the moment TR (rotating with the R side directed toward the proximal side in the drawing) around the R direction with the line passing through the centers of the rivet holes 61 as a rotation center will be $TR=F3\ r3=Fr3$.

Also, the moment TL (rotating with the L side directed toward the proximal side in the drawing) around the L direction will be $TL=F1\ r1+F2\ r2+F4\ r4=Fr1+Fr2+Fr4=F(r1+r2+r4)$.

When TR and TL are compared with each other, from $r3<r1+r2+r4$, $TL>TR$ will be established.

A moment around the L direction acts so strongly on each curving piece 60 with the axis passing through the rivet holes 61 as a rotation center that the curving piece 60 is easily rotated in the L direction.

In this embodiment, it has been explained that the tension of the wire is the same F in the UDRL directions and the positions of the wire receivers are not the same as r1 to r4. However, without being limited to it, if the moment TL around the L direction acting to separate from the fluid tube path can be made to be above the moment TR around the R direction, the values of F and r may be varied in any way.

The other formations are the same as in the first embodiment and therefore shall be omitted here.

By varying the degree of tension during a curving operation, for example, to be larger, the value of the curvature angle at which the tendency of being curved and twisted appears can be made an angle less than the maximum curvature angle. In case a large tension is required, the curving may be driven with electric driving force such as that of a motor.

The operation shall be explained below.

UDRL curving wires subjected to the tensions of F1, F2, F3 and F4 in the UDRL direction in the natural state, a moment TR (rotating with the R side directed to the proximal side in the drawing) around the R direction with the axis connecting the rivet holes 6 as a rotation center by the distances r1, r2, r3 and r4 from the rivet holes 61 of the UDRL side wire receivers supporting these wires and a moment (rotating with the L side directed to the proximal side in the drawing) around the L direction are made in the curving piece 60.

Here, because the tensions F1 to F4 in the respective directions are all of the same size F and the relations of the distances r1 to r4 are r3<r1+r2+r4, from TR=Fr3 TL=F (r1+r2+r4), TL>TR will be established and the curving piece 60 is therefore easy to move in the L direction. In the stationary state, the curving piece will not move due to friction but, in the forcibly curving moving state, it will move a little in the L direction.

Here, if curving is applied in the U direction the curving part will be curved in the U direction while gradually falling in the L direction. That is to say, in this embodiment, in case even the cover endoscope 2B itself is operated to be curved in the U direction, the U side of the curving part will be twisted to the U side and the R side will be curved to the U side while being twisted to the D side.

Therefore, this cover endoscope as inserted through the endoscope inserting channel of the cover is as in FIG. 17. In case the operation of curving in the U direction, that is, the operation of pulling the U side curving wire 62 is made, the cover endoscope side curving part 20 will be curved and twisted as described above, the cover side cover inserting part 11A will also be similarly curved and twisted and the fluid tube path will be curved as moved outside toward the maximum curvature angle.

In FIG. 17, as explained in the first embodiment, by making the cover wall thickness on the fluid tube path housing channel 50 side larger than the cover wall thickness on the endoscope inserting channel 34 side, the cover inserting part 11A is set to be of a character that the fluid tube path housing channel 50 side is easier to curve than the endoscope inserting channel 34 side and therefore a larger effect can be expected. However, in this embodiment, even if the cover wall thickness is not varied, the effect will be obtained.

As explained with reference to FIG. 2, pivoting rotatably in the direction (in this case, the U direction) in which the maximum curvature angle is generated and the reverse direction (in this case, the D direction) are the rivets 73. Pivoting rotatably in the directions (in this case, the RL directions) intersecting at right angles with the direction in which the maximum curvature angle is generated are the rivets 74. As explained in FIG. 16, the rotation moment around the axis passing through the rivets 74 will be easy to curve on the L side in the case of the cover endoscope. In the same manner, the rotation moment around the axis passing through the rivets 74 will be easy to curve on the L side also in the case of the cover inserting part 11A.

Therefore, in the case of making an operation of curving near to the maximum curvature angle in the direction in which the maximum curvature angle is generated, the rotation moment will act in the direction in which the side on which the fluid tube path in the direction intersecting substantially at right angles with the direction of the maximum curvature angle and the reverse direction is housed moves to outside the curvature and the radius of curvature on the fluid tube side will become larger (than in the case of not moving to outside the curvature). Therefore, the fluid tube path will be prevented from buckling.

The elements and features are the same as in the first embodiment and therefore shall be omitted here.

The direction having the highest using frequency is also the U direction and acts the same as the direction in which the maximum curvature angle is generated.

The fifth embodiment shall be explained below. In the fifth embodiment, the cover endoscope in the first embodiment has the maximum curvature angle in the U direction and, at the same time, the arrangements of the endoscope inserting channel 34 and fluid tube path housing channel 50 within the cover and of the fluid tube paths within the fluid tube path housing channel 50 are changed.

The same other components shall bear the same reference numerals and shall not be explained here.

Figure 18A:
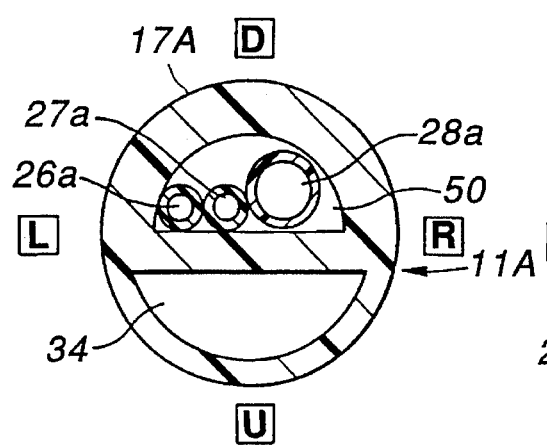
FIGS. 18a and 18b are cross-sectional views showing an inserted part cover part in the fifth embodiment of the present invention.
Figure 18B:
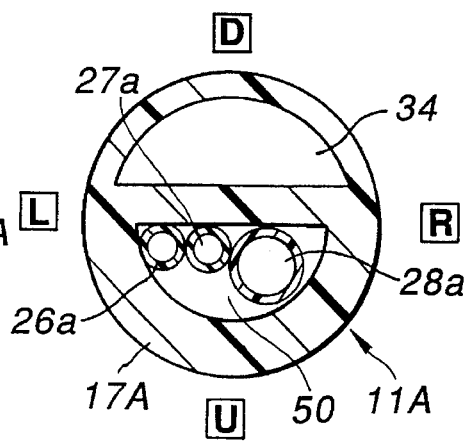

FIGS. 18a and 18b are cross-sectional views of the inserted part cover part 11A in this fifth embodiment.

In the drawings, the U, D, R and L correspond respectively to the up, down, right and left directions. The endoscope inserting channel 34 is arranged on one side of the D direction and the fluid tube path housing channel 50 is arranged on the other side. In FIG. 18a, the endoscope inserting channel 34 is provided on the U (up) side within the outer cover 17A of the inserted part cover part 11A and the fluid tube path housing channel 50 is provided on the D (down) side.

On the other hand, in FIG. 18b, the fluid tube housing channel 50 is provided on the U side within the outer cover 17A of the inserted part cover part 11A and the endoscope inserting channel 34 is provided on the D side.

In both drawings, within the fluid tube path housing channel 50, the air feeding tube path 26a, water feeding tube path 27a and sucking tube path 28a are provided in the order from the L (left) side, with the sucking tube path 28a, which is most likely to buckle, being arranged on the R side and not in the middle.

These tube paths are made of polytetrafluoroethylene having a smooth surface but weak in bending, as in the first embodiment.

Here, each of the air feeding tube path 26a and water feeding tube path 27a is a tube path 1 mm in the inside diameter and 0.2 mm thick and the sucking tube path 28a is a tube path 3 mm in the inside diameter and 0.2 mm thick.

The sucking tube path 28a has the same thickness and is larger only in the inside diameter (or outside diameter) as compared with the air feeding tube path 26a and water feeding tube path 27a and is therefore hard and more difficult to bend.

On the other hand, when the radius of curvature inside the bend is small, the sucking tube path 28 will be more likely to buckle than the air feeding tube path 26a and water feeding tube path 27a. Here, because a therapeutic treatment is made with forceps, the sucking tube path 28a is particularly important.

The outer cover 17A is constructed of material which is softer than the above-mentioned air feeding, water feeding and sucking tube paths and strong in bending as, for example, urethane rubber, silicone rubber or elongated polytetrafluoroethylene and is not likely to buckle.

The operation shall be explained below.

When the cover type endoscope is put into the endoscope inserting channel 34 and is curved in the U direction, the outer cover of the inserted part cover part 11A will be also curved in the U direction.

At this time, in FIGS. 18a and 18b, the fluid tube path housing channel 50 will be subjected to bending and, at the same time, the internal air feeding tube path 26a, water feeding tube path 27a and sucking tube path 28a will be also subjected to bending.

The sucking tube path 28a is relatively hard and is difficult to bend and the air feeding tube path 26a and water feeding tube path 27a are softer and easier to bend than the sucking tube path 28a.

When curving is applied in the U direction, at the time when it becomes difficult to compress the sucking tube path 28a, the air feeding and water feeding tube path side will be twisted so as to be inside and the sucking tube path side will be twisted so as to be outside.

As a result, the bending R inside the sucking tube path 28a will become so large so as not to be damaged so much.

In this embodiment, the sucking tube path 28a is formed to have the largest diameter and prone to buckling but, without being limited to this, the other tube paths having large diameters can be formed similarly.

The effects of this embodiment are as follows.

The damage to the tube path likely to buckle within the fluid tube path housing channel 50 can be reduced and the buckling can be prevented.

As explained above, according to the first to fifth embodiments, when the bending of the cover endoscope reaches the maximum curvature angle, the inserted part cover part will escape in the direction in which the radii of curvature inside the air feeding, water feeding and sucking tube paths and particularly the sucking tube path will become large and therefore the air feeding, water feeding and sucking tube paths will be difficult to buckle.

Even if the curving part is largely curved, the tip part will escape, therefore the inserted part cover part intercepting the observing visual field will move to either of the right and left from the center of the visual field and the observing visual field will be always secured.

The embodiment in which it can be confirmed that the cover can be fitted as not twisted shall be explained in the following. Even in the endoscope of the endoscope cover system, for the endoscope inspection, the outside diameter of the inserted part had better be as small as possible. That is to say, the smaller the diameter, the smaller the pain to the patient in the case of inserting the inserted part. In the endoscope of the endoscope cover system, after the endoscope inspection, the used cover will be abandoned and the durability may be lower than of the repeatedly used endoscope. The cover to be used may be thin.

When the cover is thin, it is easily twisted. If the cover endoscope is fitted with the cover as twisted, a twisting force will be applied to the cover, and the cover will break into the thin area. The cover endoscope, which will not always be clean, will be exposed within the body of the patient and the patient will be likely to be affected. Therefore, it has been necessary to operate carefully not to fit the cover as twisted. The following embodiment has realized a cover system endoscope wherein, even in case the cover is thin, breakage of the cover will be able to be prevented.

The sixth embodiment of the present invention shall be explained with reference to FIGS. 19 to 27.

Figure 19:
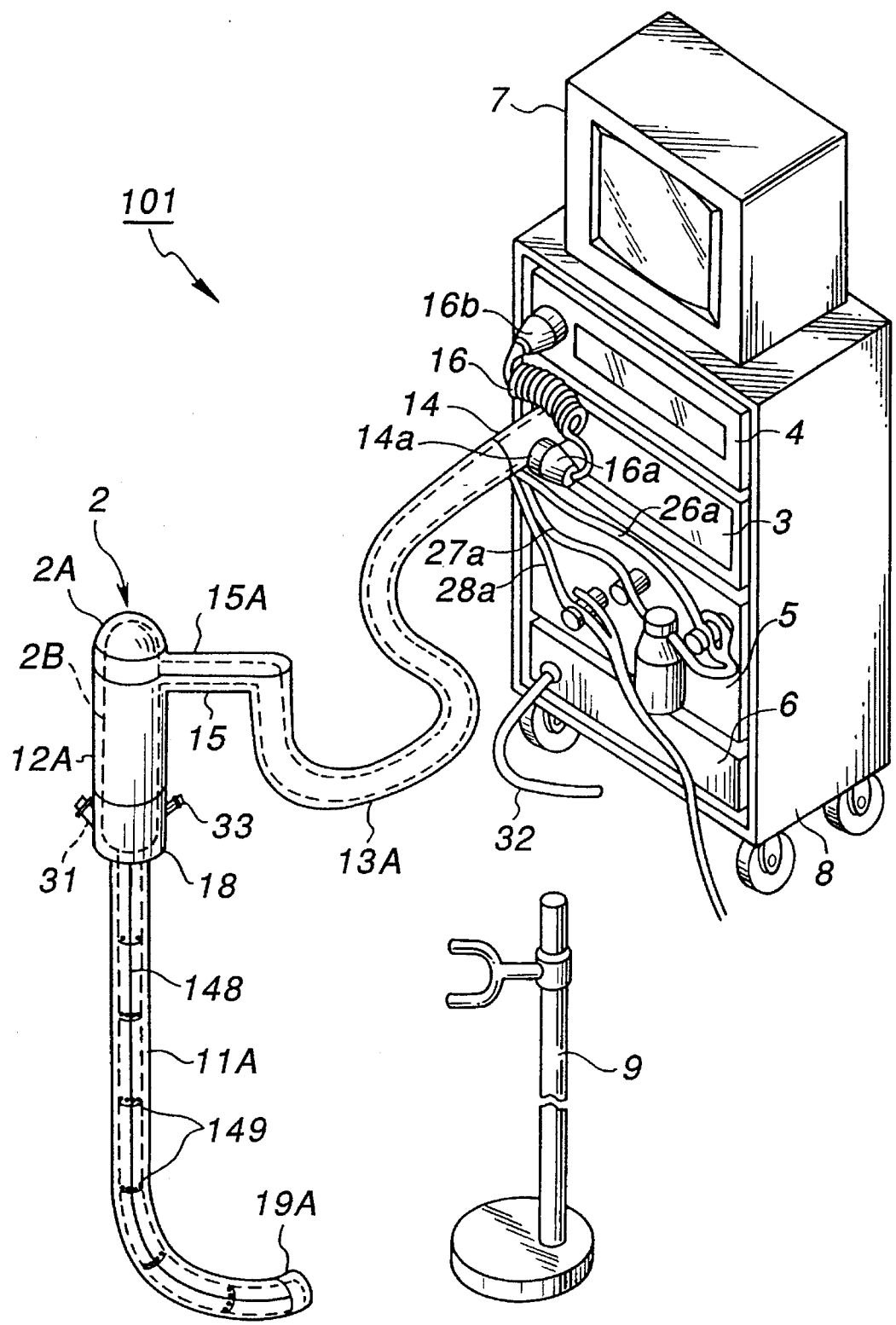
FIGS. 19 to 27 relate to the sixth embodiment of the present invention.

As shown in FIG. 19, an endoscope apparatus 101 of an endoscope cover system comprises the endoscope 2 of the cover system of the sixth embodiment consisting of the cover 2A and the cover endoscope 2B fitted to this cover 2A, a light source apparatus 3 feeding an illuminating light to this cover endoscope 2B, a video processor 4 processing signals for an imaging means built-in in this cover endoscope 2B, a fluid controlling apparatus 5 feeding air and water through the tubes of the cover 2A, a cover expander 6 used to fit the cover endoscope 2B to the cover 2A and a monitor 7 displaying video signals processed by the video processor 4. The light source apparatus 3, video processor 4, fluid controlling apparatus 5 and cover expander 6 are housed in a cart 8 and the monitor 7 is mounted on the upper surface of the cart 8.

Figure 23:
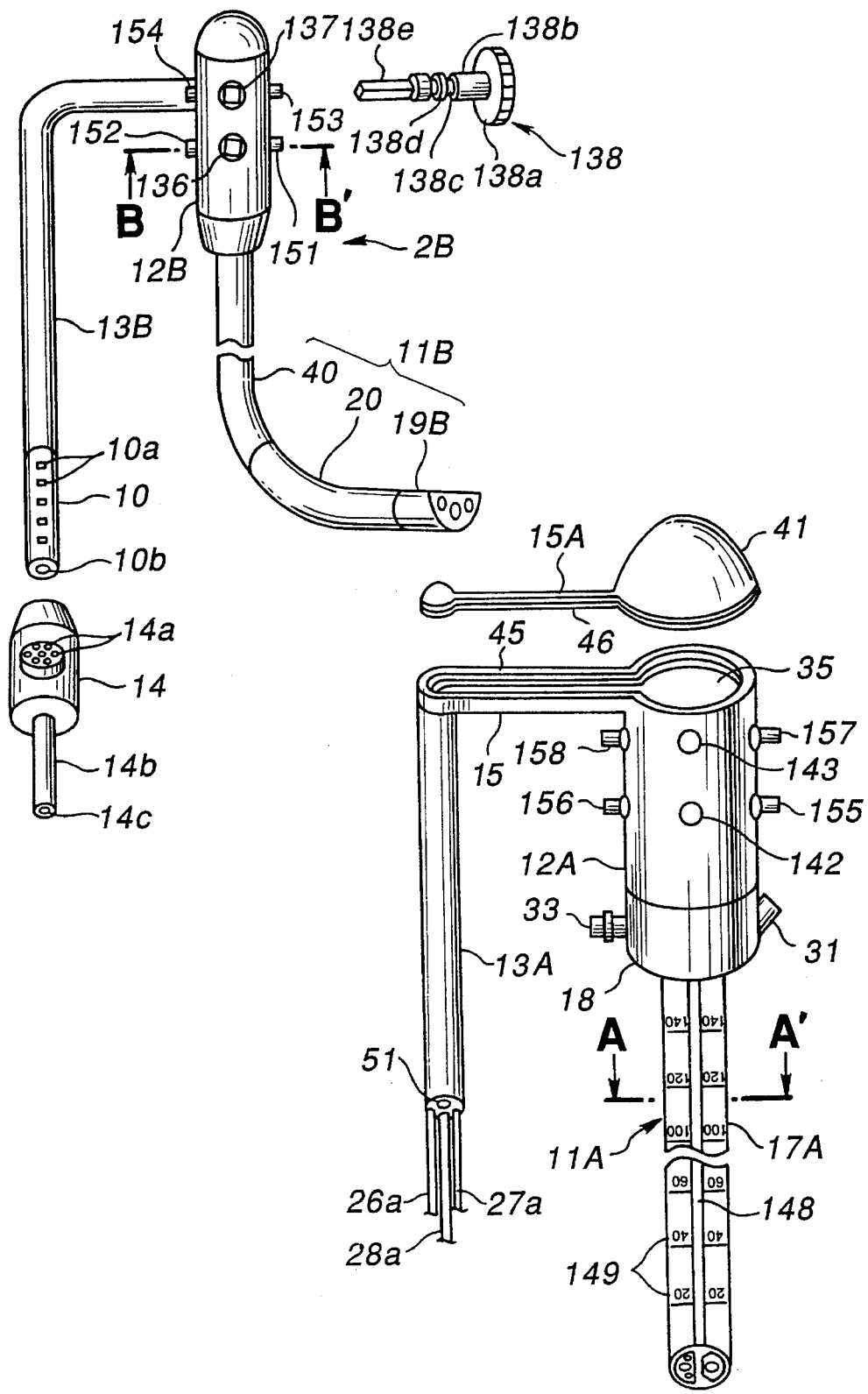

In this embodiment, FIGS. 19 and 23 show a white line 148 used as a display for making it possible to see whether or not the curving part is twisted in the axial direction and inserted length indicators 149 showing the inserted lengths are printed and provided on the outer surface of the cover inserting part 11A of the cover 2A.

Figure 20:
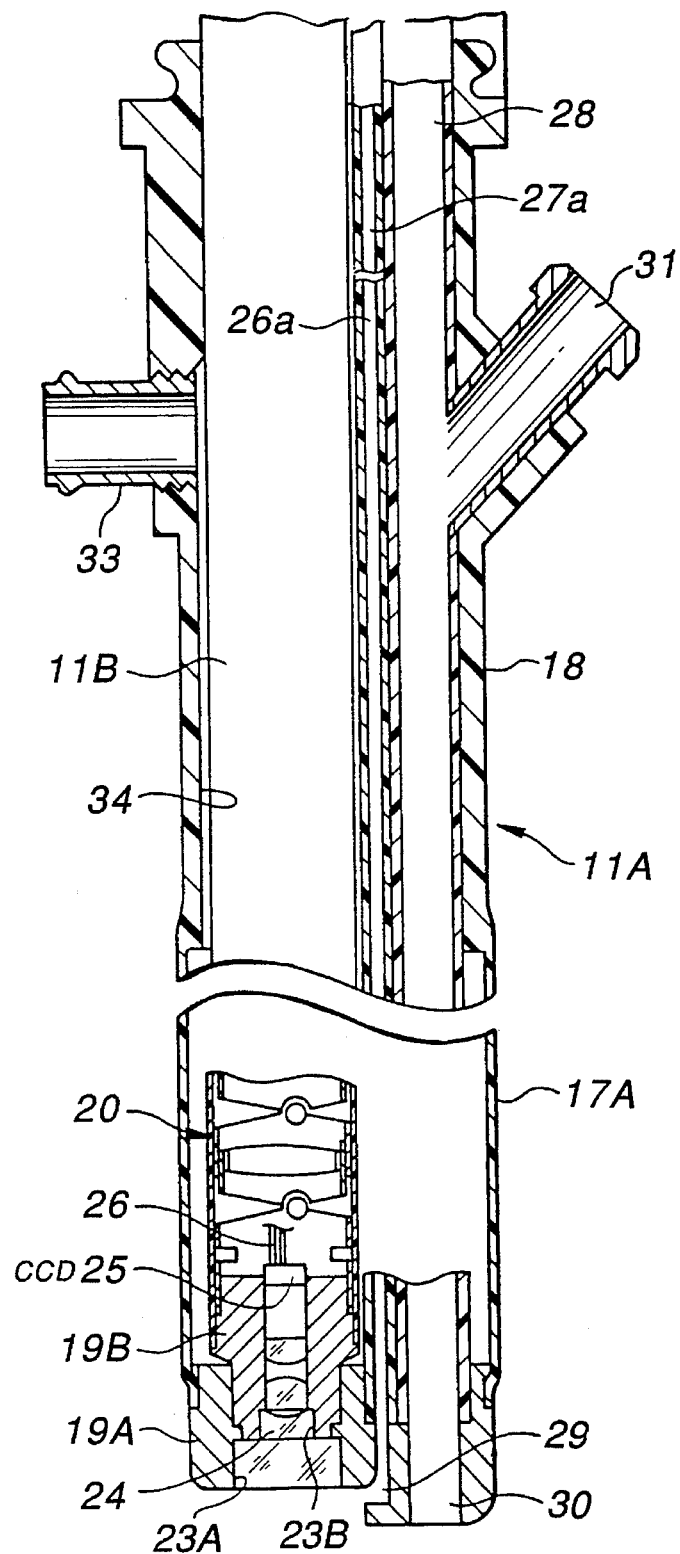
Figure 21:
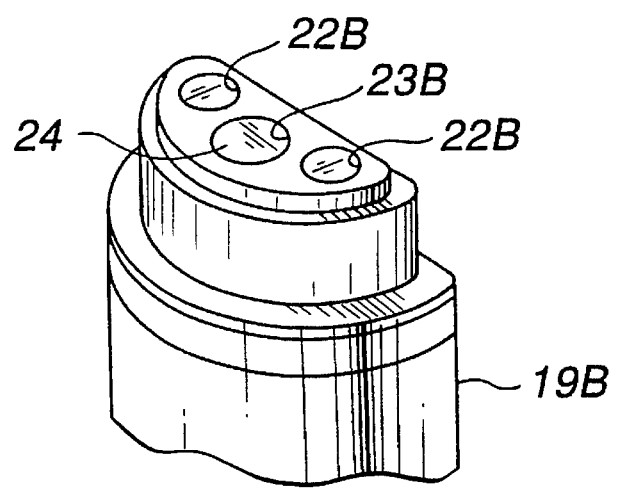
Figure 22:
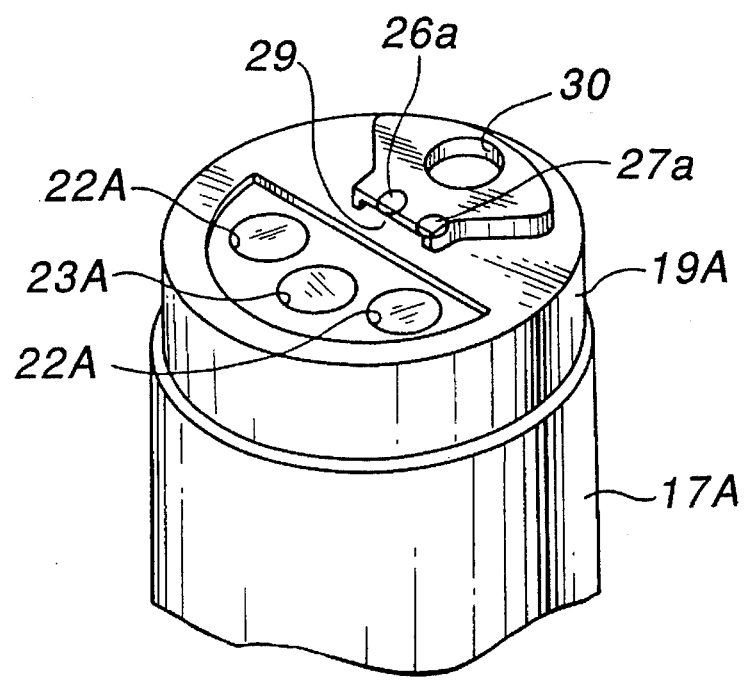

The light source apparatus 3, video processor 4 and others shown in FIG. 19 have the same formations as in the first embodiment. FIG. 20 shows as magnified the cover system endoscope 2 part in FIG. 19. The structure shown in FIG. 20 is substantially the same as in FIG. 2. The tip part 19B of the cover endoscope 2B and the cover tip part 19A of the cover 2A are as shown, respectively, in FIGS. 21 and 22 and are substantially of the same structures as are shown in FIGS. 2 and 3.

In this embodiment, the curving operating mechanism is different from that of the first embodiment. As shown in FIG. 23, two knob holes, that is, an up and down curving operating knob hole (which shall be briefly mentioned hereinafter as a UD knob hole) 136 and a right and left curving operating knob hole (which shall be briefly mentioned hereinafter as an RL knob hole) 137 are provided adjacently in the up and down directions in the operating part 12B of the cover endoscope 2B. In the case of removing the UD knob 138 and RL knob fitted respectively to the knob holes 136 and 137, they can be removed by simultaneously respectively operating two switches 151 and 152, 153 and 154.

In the sixth embodiment, the cover endoscope 2B can be curved in the four directions of the up, down, right and left (UDRL) directions respectively by 180, 180, 160 and 160 degrees, the same as in the first embodiment, for example, by the endoscope for lower digestion tubes, where the U direction is used most often.

The inserted part cover outer cover 17A of the inserted part cover part 11B is not required to be smoother on the surface than the fluid tube path and is therefore made of such soft material strong in bending as, for example, urethane rubber, silicone rubber or elongated polytetrafluoroethylene. Also, the inserted part cover outer cover 17A is made thin from the endoscope inserting channel 34 to the outer periphery but is thick elsewhere. The flexibility in the left direction is made high and the flexibility in the right direction in which the fluid tube path housing channel 41 is located is made low.

Therefore, in case the fluid tube path is curved in the direction of the maximum curvature angle, as in the first embodiment, it will be curved and twisted to escape to the outside of the curvature, and will have a large radius of curvature and will be prevented from buckling.

Figure 24:
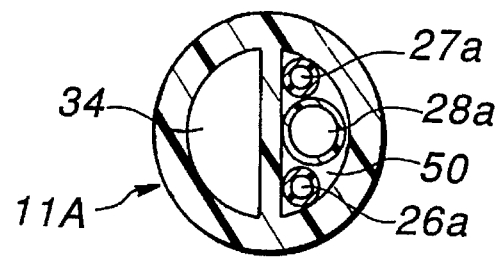

As shown in FIG. 24, the endoscope inserting channel 34 is semi-circular in cross-section, the same as in the first embodiment, so as to be insertable through the inserted part 11B of a semi-circular cross-section. The air feeding tube path 26a, water feeding tube path 27a and sucking tube path 28a are housed within the fluid tube path housing channel 50 semi-circular in the cross-section.

These tube paths inserted through the inserted part cover part 11A (its fluid tube path housing channel 50) are inserted through the operating part cover part 12A, are further inserted through the bridge 15 and universal cord 13A and are extended out of the distal end of the universal cord 13A, as shown in FIG. 23.

Further, as shown in FIG. 23, the operating part cover part 12A is provided with holes 142 and 143 in the positions corresponding to the UD knob hole 136 and RL knob hole 137 of the operating part 12B. Therefore, for example, when the cover endoscope 2B is covered with the cover 2A, the UD knob 138 will be able to be fitted to or removed from the cover endoscope 2B through the hole 142 and UD knob hole 136. It will also be the same on the RL knob.

On the inside surface of the operating part cover part 12A and bridge 15, a recess 45 is provided, as in the first embodiment. On the outer periphery of the bridge cover 15A, a projection 46 is provided so that, when the bridge cover 15A is pushed into the operating part cover part 12A and bridge 15 side, both will be connected to each other.

A universal cord inserting tube path 51 having a diameter larger than the outside diameter of the universal cord 13B is provided within the universal cord 13A. A groove in which the universal cord 13B can be housed is also provided in the bridge 15.

As described above, in this embodiment, as shown in FIG. 23, a straight white line 148 is provided over the entire length in the axial direction of the inserted part cover part 11A so as to be able to see whether or not the inserted part cover part 11A is twisted. Inserted length indicators 149 arranged at regular intervals and showing the inserted lengths from the tip of the cover tip part 19A are printed on the surface of the inserted part cover part 11A. Therefore, in case the inserted part cover part 11A is twisted, the white line 148 and inserted length indicators 149 will also be twisted.

Further, this embodiment is provided with a mechanism of removably fitting an RL knob (not illustrated) of the same structure as of the UD knob 138. As shown in FIG. 23, the UD knob 138 comprises a disc part 138a and a shaft part 138b.

The shaft part 138b is provided with grooves 138c and 138d and is made a square pillar part 138e in the end part.

UD knob switch covers 155 and 156 and RL knob switch covers 157 and 158 are provided where the UD knob switches 151 and 152 and RL knob switches 153 and 154 of the cover endoscope 2B of the operating part cover part 12A are located.

Figure 25:
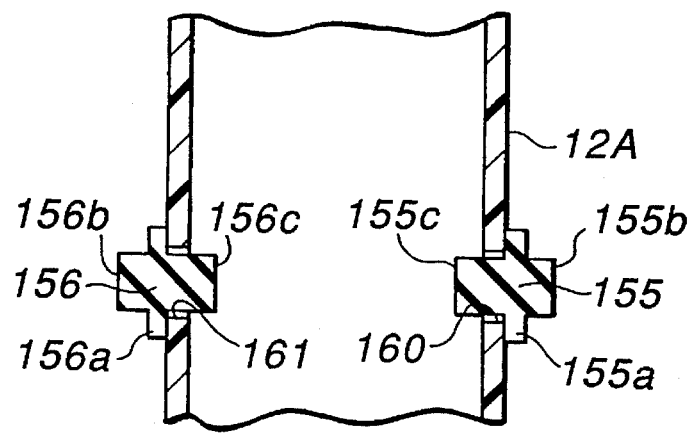

As shown in FIG. 25, the UD knob switch covers 155 and 156 made of an elastic material are put from outside into holes 160 and 161 provided in the hard operating part cover part 12A and flanges 155a and 156a are connected to the operating part cover part 12A.

Here, when finger pushed parts 155b and 156b are pushed to the middle side in FIG. 25, the flanges 155a and 156a will be transformed and the SW pushing parts 155c and 156c will project toward the middle in FIG. 25. The RL side, not illustrated, is similarly arranged.

Figure 26:
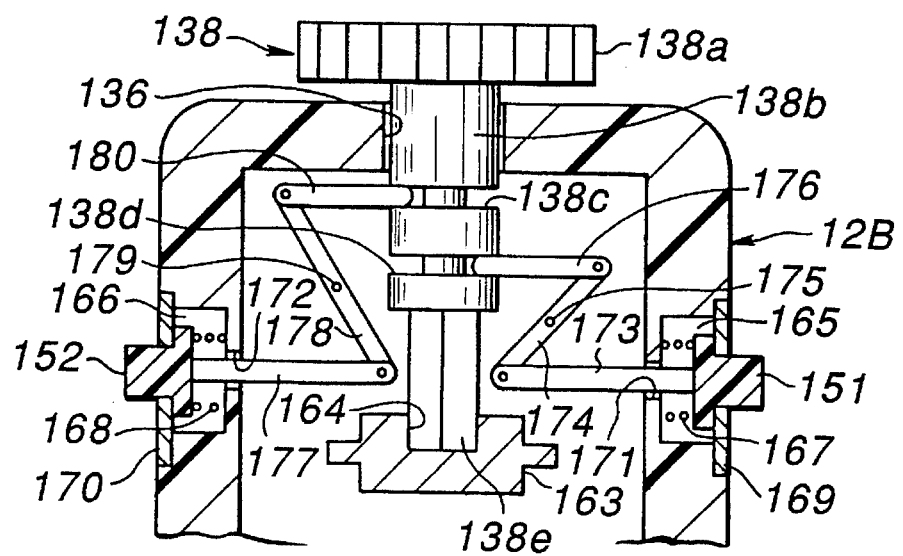

FIG. 26 is a view showing a cross-section on line B–B' in FIG. 23 of the UD knob 138 as inserted into the UD knob hole 136.

In FIG. 26, a chain, not illustrated, is wound on a sprocket 163 and a wire, not illustrated, is connected to the chain at the end and is connected to a curving piece, not illustrated, at the tip of the inserted part 1B of the cover endoscope 2B in FIG. 23.

The sprocket 163 has a square hole 164 in which the square pillar part 138e of the UD knob 138 is fitted so that, when the UD knob 138 is rotated, the sprocket 163 will rotate.

The operating part 12B has counter-sunk holes 165 and 166 in which the UD knob switches 151 and 152 are respectively inserted by holding compression springs 167 and 168. Removal preventing rings 169 and 170 are fitted to the operating part 12B to prevent the UD knob switches 151 and 152 from expanding.

The above-mentioned counter-sunk holes 165 and 166 respectively have through holes 171 and 172 through which cranks 173 and 177 are respectively inserted.

Here, the crank 173 is fixed at one end to the UD knob switch 151 and is connected rotatably at the other end with the crank 174. The crank 174 is provided in the middle with a rotation center pin 175 rotatably supported in the operating part 12B.

The crank 174 is rotatably connected at the other end with a crank 176 which is inserted at the end into the groove 138d of the UD knob 138.

The crank 177 is fixed at one end to the UD knob switch 152 and is connected at the other end rotatably with a crank 178 which is provided in the middle with a rotation center pin 179 rotatably supported in the operating part 12B.

The crank 178 is rotatably connected at the other end with a crank 180 and is inserted at the end into the groove 138c of the UD knob 138.

The cranks 176 and 180 are removal preventives in the up direction in FIG. 26 of the UD knob 138.

Figure 27:
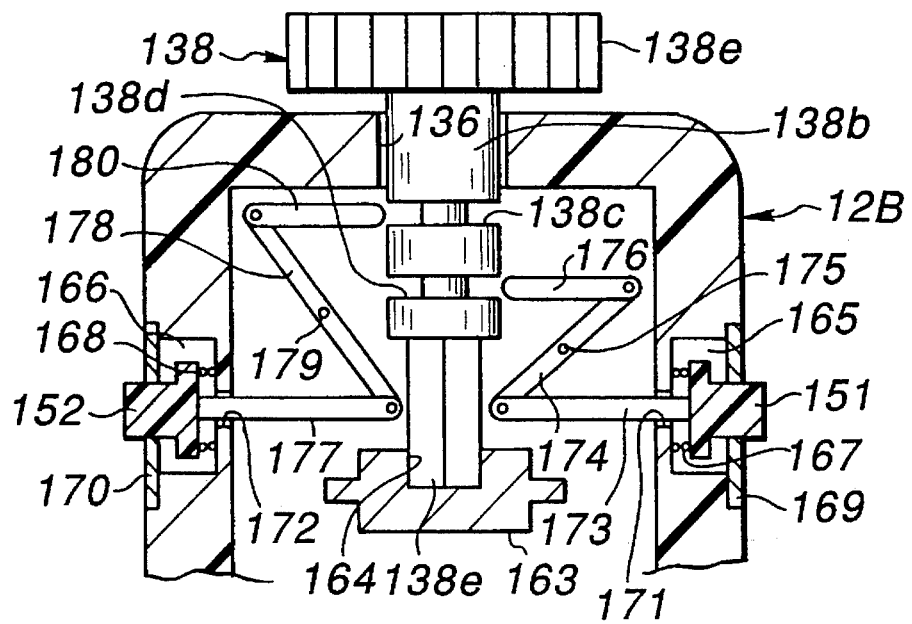

FIG. 27 is a view of the UD knob switches 151 and 152 as pushed in.

When the UD knob switch 151 is pushed, the crank 173 will move at the end in the left direction in FIG. 26 to be as in FIG. 27, the crank 174 will rotate clockwise with the rotation center pin 175 as a center and the crank 176 will move in the right direction in the drawing and will be pulled out of the groove 138d.

In the same manner, when the UD knob switch 152 is pushed, the crank 177 will move at the end in the right direction in FIG. 26 to be as in FIG. 27, the crank 178 will rotate counter-clockwise with the rotation center pin 179 as a center and the crank 180 will move in the left direction in the drawing to be pulled out of the groove 138c.

In this embodiment, the endoscope inserting channel 34 has a circular cross-section but is not limited to this and may have a square or triangular cross-section. Also, the displays on the outer fitting of the inserted part cover part 11A need not be both of the white line 148 and inserted length indicators 149 but may be either one. The color of the line is not limited to white but may be any other color.

The inserted length indicators may be characters. A plurality of or more than three knob switches may be provided per knob.

The operation of the sixth embodiment shall be explained below. The procedures from the fitting of the cover 2A to the end of the inspection shall be explained in the following.

In FIG. 19, the cover holder 9 is covered with a cover holder cover, not illustrated, and then the endoscope fixing mouth body part 18 of the cover 2A is set.

The switch of the cover expander 6 is engaged so that air may be fed from the open end of the expanding tube 32.

The expanding tube 32 is fitted to the expanding tube mouth body 33 of the cover 2A so that air may be fed into the endoscope inserting channel 34 in FIG. 6 and the endoscope inserting channel 34 may expand.

Here, the cover endoscope 2B inserting part 11B is inserted into the endoscope inserting channel 34. When the endoscope inserting channel 34 has expanded, the inserted part 11B can be smoothly inserted and the endoscope inserting channel 34 is not circular but has a different cross-sectional shape and will be therefore twisted so that it is difficult to house when it is fitted.

In case the inserted part 11B is to be inserted into the inserted cover part 11A, if the inserted part cover part 11A is twisted, the white line 148 printed to be straight in the axial direction over the entire length and the inserted length indicators 149 on the outer fitting of the inserted part cover part 11A will be twisted and therefore the twist will be easy to recognize.

When the twist is recognized, the inserted part cover 11A will be made straight and the inserted part 11B will be replaced.

As in FIG. 20, the tip part 19B of the inserted part 11B is set at the tip of the inserted part cover part 11A, the operating part 12B is also set and the expanding tube 32 is removed.

At this time, in FIG. 23, the UD knob hole 136 and RL knob hole 137 will be positioned respectively inside the holes 142 and 143 of the operating part cover part 12A.

The UD knob switches 151 and 152 and RL knob switches 153 and 154 are positioned respectively inside the UD knob switch covers 155 and 156 and RL knob switch covers 157 and 158.

Here, when the UD knob switch covers 155 and 156 are pushed, the SW pushing parts 155c and 156c in FIG. 25 will push the UD knob switches 152 and 153 in FIG. 26.

Then, as in FIG. 27, the cranks 176 and 180 will retreat from the middle in the drawing.

By the way, in FIGS. 26 and 27, the operating part cover part 12A is omitted.

In this state, the UD knob 138 is inserted into the hole 142 and UD knob hole of the operating cover part 12A.

Then, the square pillar part 138e of the UD knob 138 will be inserted into the square hole 164 of the sprocket 163 and both will be fitted to each other and will be able to rotate together.

Here, when the hand is separated from the UD knob switch cover 155 and 156, the UD knob switches 151 and 152 will be returned by the compression springs 167 and 168 until they contact the removal preventing rings 169 and 170 as shown in FIG. 26. Thus the cranks 176 and 180 will be inserted respectively into the grooves 138d and 138c of the UD knob 138 so that the UD knob 138 will not be removed in the up direction.

The RL knob can also be fitted in the same manner.

Then, the universal cord 13B shown in FIG. 23 is inserted into the universal cord inserting tube path 51 of the universal cord cover part 13A.

The universal cord inserting tube path 51 is a hole larger than the universal cord 13B and therefore the universal cord 13B can be smoothly inserted.

At this time, the universal cord connector 10 of the universal cord 13B will project out of the universal cord cover part 13A.

Here, the connector adapter 14 is fitted to the connector 10.

Then, the illuminating light incident end 14c and the illuminating light incident end 10b of the cover endoscope 2B will optically connect with each other and the illuminating light incident end 14c and the illuminating optical system provided in the tip part 19B of the inserted part 11B of the cover endoscope 2B will be optically connected to one other.

Also, the electrical contact 10a of the cover endoscope 2B will electrically connect with the video processor connector 16a.

When the tube part 14b is connected to the light source apparatus 3 in FIG. 19, the illuminating light will be led to the illuminating optical system.

When the video processor connector 16a is connected to the video processor 4 through the cable 16, as shown in FIG. 19, the image from the objective optical system 24 in FIG. 23 will be converted to an electrical signal by the CCD 25. The electrical signal will then be led to the video processor in FIG. 1 and will be converted here to a video signal and the video signal will be displayed in the monitor 7.

Here, the bridge cover 15A is pressed against the operating cover part 12A and bridge 15. Then, the projection 46 on the outer periphery of the bridge cover 15A and the recess 45 on the inside surface of the operating part cover part 12A and bridge 25 will engage and connect with each other.

The air feeding tube path 26a, water feeding tube path 27a and sucking tube path 28a projecting out of the universal cord part 13A are connected to the fluid controlling apparatus 5 in FIG. 1. In this state, the endoscope inspection can be made.

In the endoscope inspection, whenever it is desired that the inserted part cover part 11B shown in FIG. 23 is to be curved in the U (up) direction, the UD knob 138 in FIG. 26 will be rotated in the direction corresponding to the U direction.

Then, the sprocket 163 will also rotate and the curving piece (not illustrated) at the tip within the inserted part 11B of the cover endoscope 2B within the insert part cover part 11B in FIG. 23 will be pulled through the chain wire (not illustrated) wound on this sprocket 163.

Then, the inserted part 11B will curve at the tip substantially in the U direction and the inserted part cover part 11A will also curve substantially in the U direction. Furthermore, as explained in the first embodiment, such fluid tube path as the air feeding tube path 26a will be curved and twisted so as to move to the outside. Therefore, the curving direction will be a direction deviating somewhat from the U direction.

When the inspection ends, in case the UD knob 138 is to be removed, when the UD knob switches 151 and 152 are pushed, as in FIG. 27, the cranks 180 and 176 will separate respectively from the grooves 138c and 138d of the UD knob 138 so that the UD knob 138 may be removed.

The case of removing the RL knob is also the same.

According to this sixth embodiment, when the endoscope inserting channel 34 within the inserted part cover part is different in the shape, the inserted part will be twisted and will be difficult to insert and the inserted part cover part 11A will be able to be effectively prevented from being fitted as twisted.

Therefore, during a curving operation during the endoscope inspection, there will be an effect of effectively preventing the inserted part cover part 11A from being broken by the twisted fitting. Also, the possibility of generating a contagious disease by the break of the cover can be reduced.

The seventh embodiment shall be explained below. In this embodiment, the endoscope inserting channel 34 of the inserted part cover part 11A in the sixth embodiment is made circular in cross-section, the inserted part 11B of the cover endoscope 2B is also made circular in cross section and furthermore, twist preventing spindles made of wires are provided within the inserted part cover part 11A.

Figure 28:
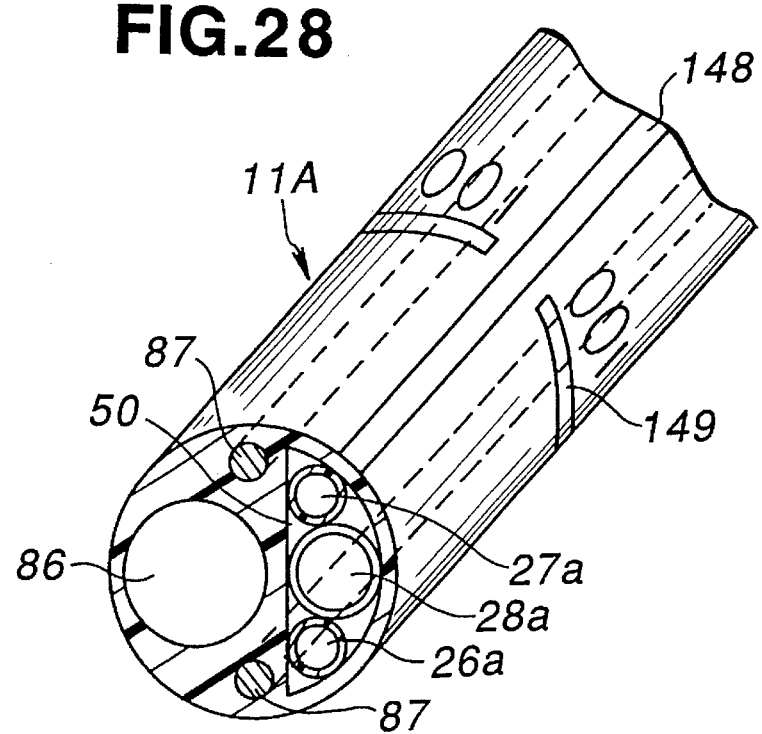
FIG. 28 is a cross-sectional view showing the structure of an inserted part cover part in the seventh embodiment of the present invention.

FIG. 28 shows the inserted part cover part 11A in this embodiment as cut on the way.

An endoscope inserting channel 86 having a circular cross-section and a fluid tube path 50 having a circular cross-section are provided within the inserted part 11B.

Two wires 87 acting as spindles for preventing twist are inserted through the entire length of the inserted part cover part 11A.

The other effects are the same as in the sixth embodiment. The same components shall bear the same reference numerals and shall not be explained here.

In the seventh embodiment, in case the inserted part is to be inserted into the endoscope inserting channel 86, even if the inserted part cover part 11A tends to twist, the wires 87 will operate to return the inserted part cover part 11A to the original state having no twist and, therefore, it will be difficult to twist.

The other effects are the same as in the operation of the sixth embodiment.

According to the seventh embodiment, as the wires for preventing twist are provided within the inserted part cover part, even if the inserted part cover part tends to twist, it will self-return and will be difficult to twist. Therefore, there is an effect of effectively preventing the generation of the breaking of the cover in making a curving operation during the endoscope inspection.

According to the sixth and seventh embodiments, when displays for visually confirming the twist of the inserted part cover part are provided in the inserted part cover part, the inserted part cover part can be prevented from when the cover is to be fitted as twisted when the cover is to be fitted to the cover endoscope and the contagion into the body of the patient from the exposure of the cover endoscope by the break of the inserted part cover part can be prevented.

An embodiment wherein the visibility can be adjusted with the cover as applied shall be explained below.

In the prior art example, with the cover applied, the visibility adjusting ring is also covered with the cover and the operation from outside the cover is difficult. Therefore, the visibility must be adjusted before the cover is fitted. However, if the operator should shift positions during the operation, it will be necessary to remove the cover and readjust the visibility. Thus, the operability is low. This defect is eliminated in the following embodiment. The same components as in the first embodiment shall bear the same reference numerals and shall not be explained here.

Figure 29:
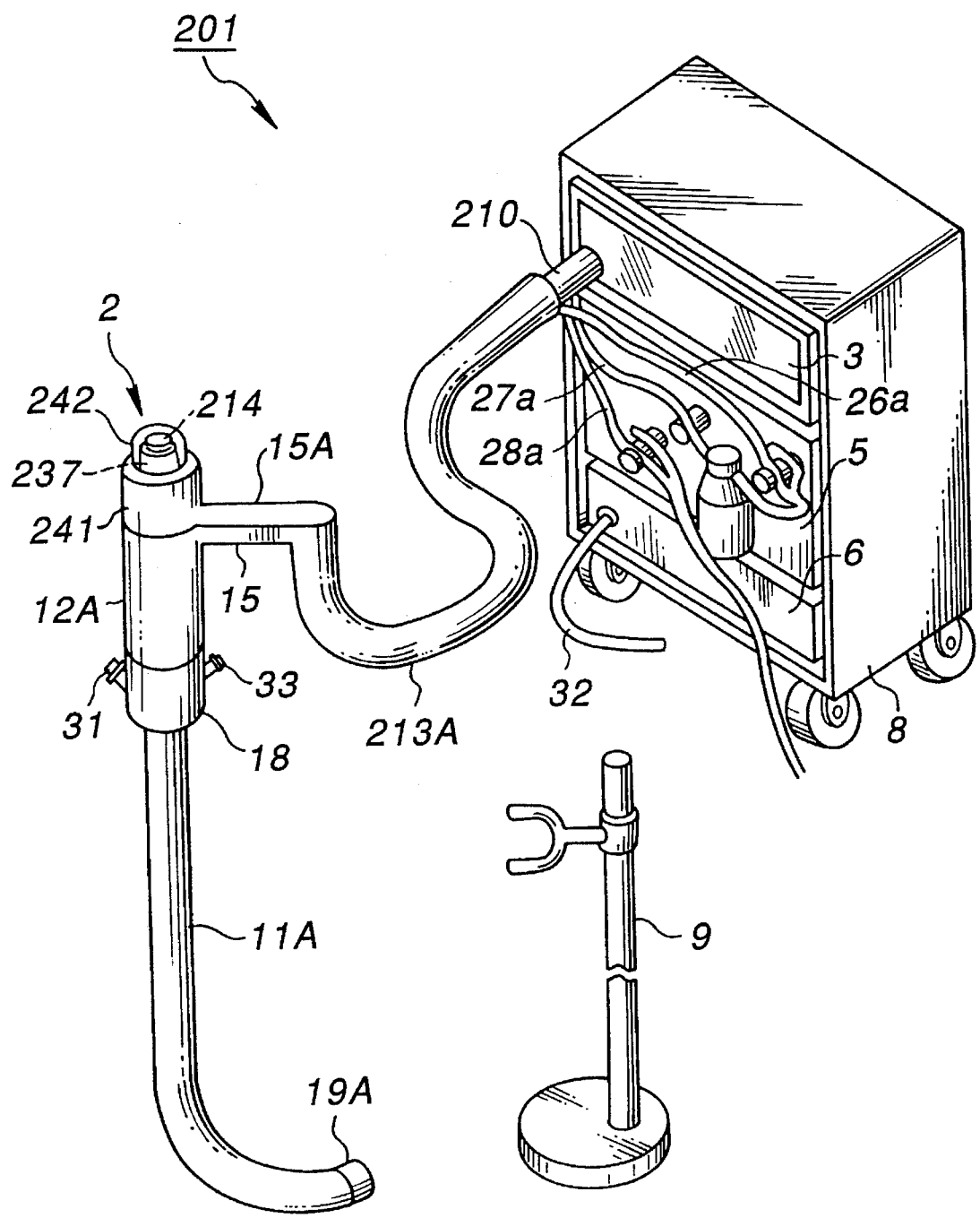
FIGS. 29 to 39 relate to the eighth embodiment of the present invention.

As shown in FIG. 29, a cover system endoscope apparatus 201 comprises a cover system endoscope 2 consisting of a cover 2A and a cover endoscope 2B fitted to this cover 2A, a light source apparatus 3 feeding an illuminating light to this cover endoscope 2B, a fluid controlling apparatus 5 feeding air and water through tubes of the cover 2A and a cover expander 6 used to fit the cover endoscope 2B to the cover 2A. The light source apparatus 3, fluid controlling apparatus 5 and cover expander 6 are housed in a cart 8.

In this embodiment, the cover endoscope 2B is an optical endoscope and the apparatus 1 shown in FIG. 1 has no video processor 4 and monitor 7. This cover endoscope 2B can be curved by 180, 180, 160 and 160 degrees respectively in the U, D, R and L directions as, for example, in the first embodiment.

Figure 30:
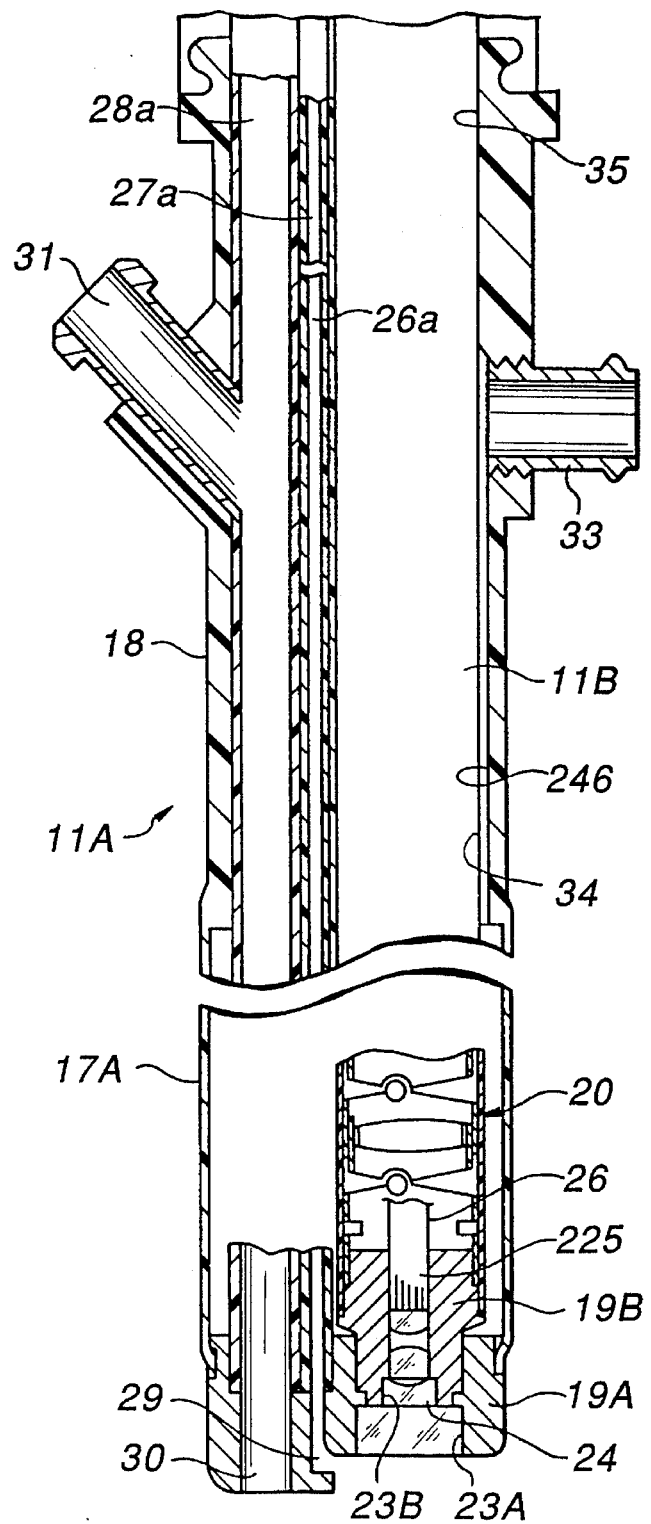
Figure 33:
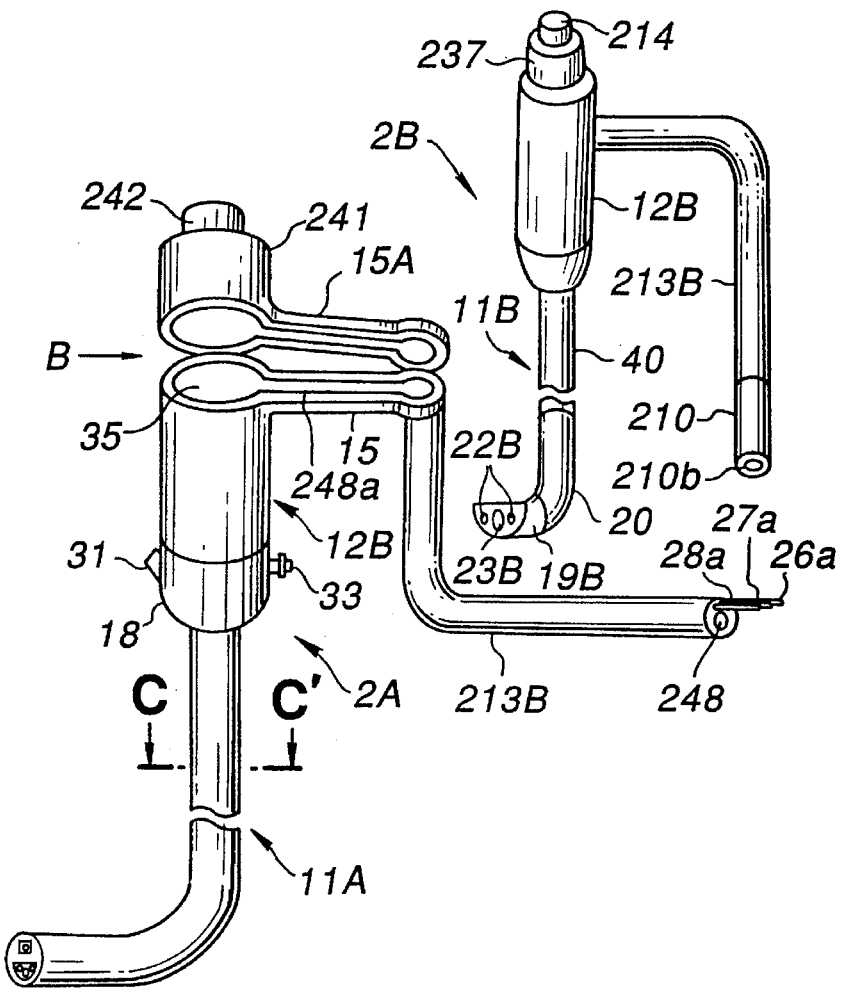

FIG. 30 shows a magnified view of the cover system endoscope 2 part in FIG. 29. FIG. 33 shows the cover system endoscope 2 with the cover and cover endoscope 2B separated from each other. In FIG. 30, the tip surface of an image guide 125 is arranged instead of the CCD 25 in the image forming position of the objective optical system 24 in FIG. 2. Also, an expanding groove 246 (see FIG. 35) projects radially outside the endoscope inserting channel 34. The others are of the same structure as in FIG. 2

As shown in FIG. 33, the cover endoscope 2B comprises an elongate and flexible endoscope inserted part (which shall be hereinafter briefly mentioned as an inserted part) 11B of a semi-circular cross-section, an endoscope operating part (which shall be hereinafter briefly mentioned as an operating part) 12B formed on the proximal end side of this inserted part 11B, a light guide cable 213B extended out of the side of this operating part 12B and an eyepiece part 214 provided with a visibility adjusting ring 237.

A light guide cable connecter 210 is provided at the distal end of the light guide cable 213B so that, when the connector 210 is removably connected to the light source apparatus 3, an illuminating light from a lamp within the light source apparatus 3 will be fed to the illuminating light incident end 210b of the connector 210.

The operating part 12B is provided with a curving operation knob (not illustrated) so that, by rotating the knob, the curving part 20 may be curved in the up, down, right and left directions.

On the other hand, the cover 2A comprises an inserted part cover part 11A and operating part cover part 12A, respectively, covering the inserted part 11B and operating part 12B of the cover endoscope 2B, a light guide cable cover part 213A covering the light guide cable 213B, a bridge 15 connecting the operating part cover part 12A and light guide cable cover part 213A to each other and a bridge cover 15A covering the upper part side of the operating part and eyepiece part 14.

The illuminating light incident upon the illuminating light incident end 210b of the connector 210 from the lamp (not illustrated) within the above-mentioned light source apparatus 3 is transmitted to the end surface on the tip side of the inserted part 11B by a light guide formed of optical fiber bundles (not illustrated).

Figure 31:
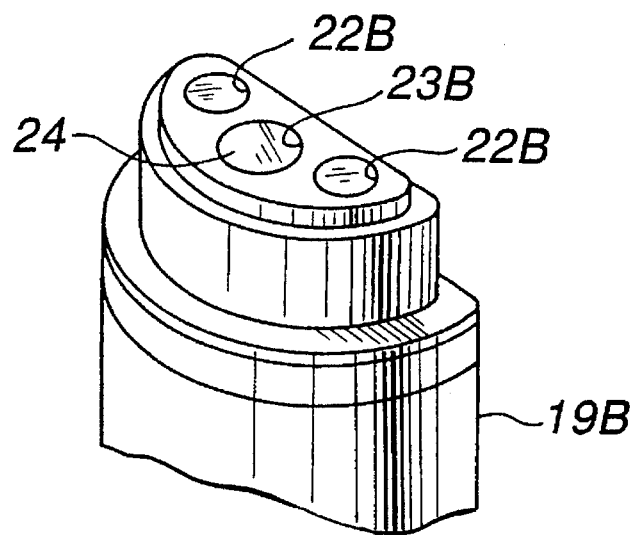

As shown in FIG. 31, the illuminating light is projected to the forward object side through an illuminating optical system fitted to illuminating windows 22B in the tip part 19B of the inserted part 11B and a transparent plate of a cover illuminating window 22A (see FIG. 33) provided to cover the illuminating optical system.

Figure 32:
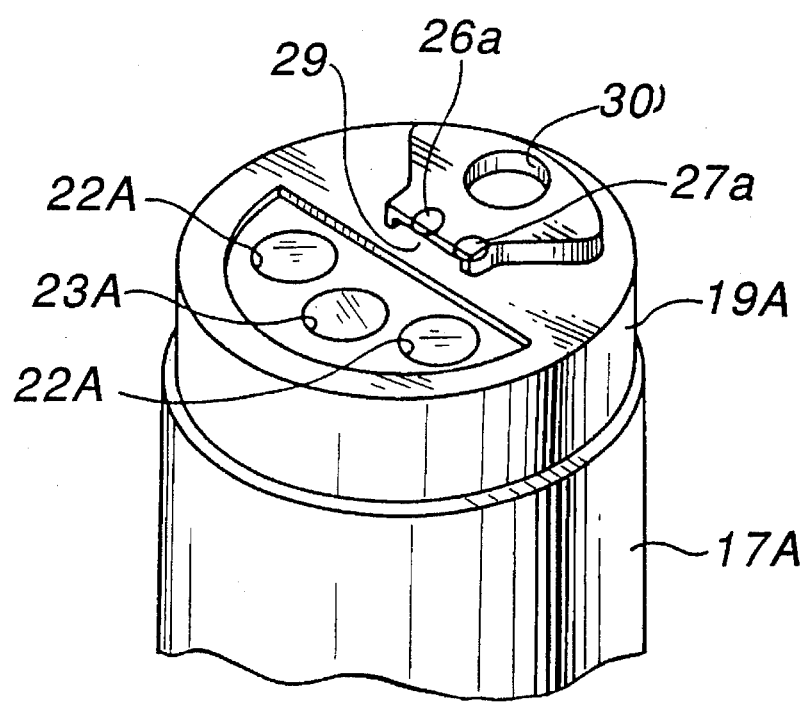

The cover tip part 19A shown in FIG. 32 has the sme structure as in FIG. 4. The optical image of the objective optical system 24 shown in FIG. 30 is transmitted by the image guide 25 to the rear end surface on the eyepiece part 214 side through the inserted part 11B and operating part 12B.

As in the sixth embodiment, the air feeding tube path 26a, water feeding tube path 27a and sucking tube path 28a are inserted through the bridge 15 and light cable guide cover part 213A from the interior of the endoscope operating part fixing mouth body part 18d, are then projected out of the tip of the light guide cable cover part 213A and are connected to the fluid controlling apparatus 5.

The operating part cap part 241 (of the bridge cover 15A) covering the upper side of the operating part 12B is further provided with an eyepiece cap 242 covering an eyepiece part 214. As described later, this eyepiece cap 242 is rotatably fitted to the operating part cap part 241.

Figure 34:
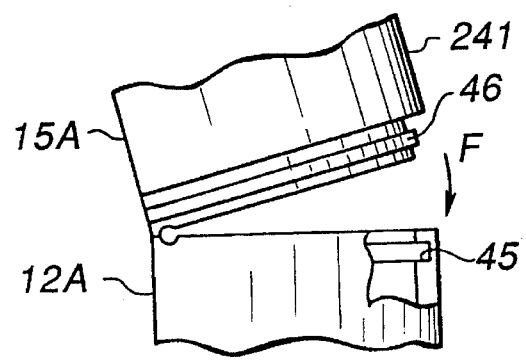

As shown in FIG. 34, which is a view as seen in the direction indicated by the arrow B in FIG. 33, the opening part 35 of the operating cover part 12A is connected in a part at the upper end with the bridge cover 15A of an elastic material through a hinge. A recess 45 is provided on the inside surface of the opening part 35 and bridge 15 of the operating part cover part 12A and, on the other hand, a projection 46 is provided at the lower end of the bridge cover 15A.

Figure 35:
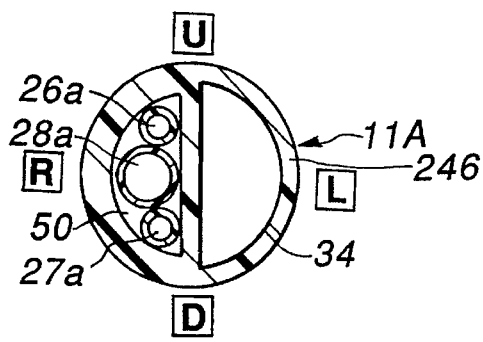

Therefore, by pressing the bridge cover 15A in the direction indicated by F in FIG. 35, the projection 46 can be housed in and connected with the recess 45. The relation between the bridge part 15 and bridge cover 15A is also the same.

FIG. 35 shows a cross-section taken along line C–C' in FIG. 33. The inserted part cover part 11A is provided within it with a chamber consisting of an endoscope inserting channel 34 of a semi-circular cross-section and an expanding groove 246 of a square cross-section to be an air path (from the expanding tube mouth body 33) projected out of this endoscope inserting channel 34 and a chamber consisting of a fluid tube path housing channel of a semi-circular cross-section.

The above-described air feeding tube path 26a, water feeding tube path 27a and sucking tube path 28a are housed within the fluid tube path housing channel 50. Even in this embodiment, as a fluid flows through these tube paths, they are made of such material smooth on the surface as, for example, polytetrafluoroethylene. Though having a smooth surface, such material is so weak in bending that, when it is subjected to a strong bending, the inside radius of curvature will become so small as to buckle.

On the other hand, the inserted part cover outer cover 17A of the inserted part cover part 11B need not be smooth on the surface and is therefore made of such soft material strong in bending as, for example, urethane rubber, silicone rubber or elongated polytetrafluoroethylene.

The inserted part cover outer cover 17A is thin from the endoscope inserting channel 34 to the outer periphery but is otherwise thick. It is high in flexibility on the L direction side but is low in flexibility on the R direction side on which the fluid tube path housing channel 50 is located. (It is harder to curve on the R direction side than on the L direction side.)

Therefore, in case it is curved in the maximum curvature angle direction (for example, the U direction), as explained in the first embodiment, such fluid tube path as the air feeding tube path 26a will be curved and twisted to move to outside the curvature.

In FIG. 33, a light guide cable inserting tube path 248 of a diameter larger than the outside diameter of the light guide cable 213B is provided within the light guide cable cover part 213A. Also, the bridge 15 is provided with a groove part 248a housing the light guide cable 213B.

To fit the cover endoscope 2B to the cover 2A, the inserted part 11B is put into the endoscope inserting channel 34, the light guide cable 13B is put into the light guide cable inserting tube path 248, then the bridge cover 15A is made to fall on the side of the operating part cover part 12A and bridge 15 and both are connected.

In this embodiment, the bridge cover 15A is connected to the operating part cover part 12A and bridge 15. However, without being limited to this, both may be separated from each other.

In such case, the bridge cover 15a and eyepiece cap 242 may be of a hard material.

Figure 36:
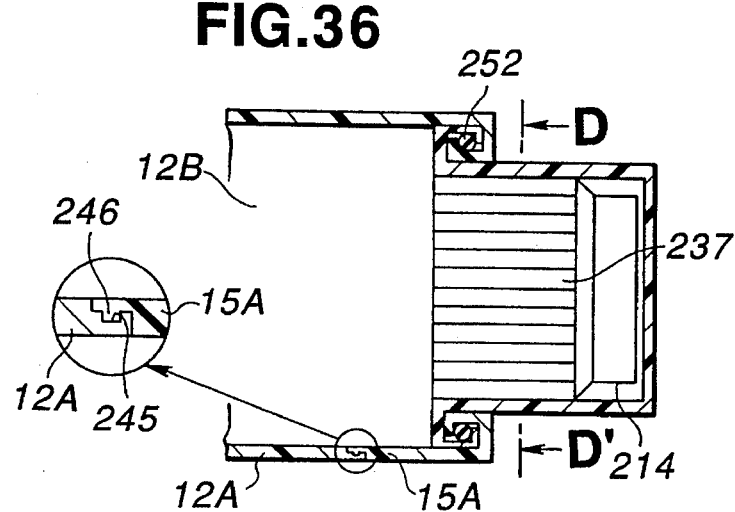

FIG. 36 is a view showing the upper end side part of the operating part 12B and the vicinity of the eyepiece part 214 of the cover endoscope 2B.

As in FIG. 36, the operating part 12B is covered with the operating part cover part 12A and (the operating part cap 241 of the) bridge cover 15A to be isolated from the external environment and the eyepiece part 214 is isolated from the external environment by the eyepiece cap 242. The eyepiece part 214 is transparent except for the lens and is made of such elastic material as, for example, a black resin.

Here, the pawl part of the proximal end of the eyepiece cap 242 and the pawl part of the upper end opening part of the bridge cover 15A are engaged with each other, the eyepiece cap 242 is rotatably connected to the bridge cover 15A and a water-proof structure is made between the bridge cover 15A and eyepiece cap 242 by an O-ring 252 housed between the pawls.

The eyepiece part 214 is provided with a visibility adjusting ring 237 which is rotated to adjust the visibility. The mechanisms on the periphery of the visibility adjusting ring 237 shall be explained in the following.

Figure 37:
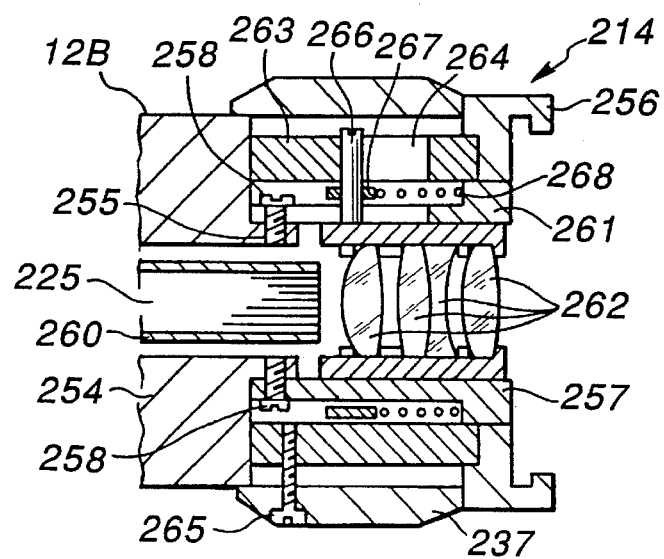

FIG. 37 is a cross-sectional view of the eyepiece part 214. In the drawing, the reference numeral 254 represents a fixing member of an image guide 225 which is an image transmitting optical system provided in the operating part 12B and an annular connector 255 is provided to project on the tip part of this fixing member 254.

A supporting barrel 257 having a large diameter part 256 formed at the tip is connected and fixed at the lower end to this connector 255 by screws 258.

The eyepiece side end part of the image guide 225 consisting of optical fiber bundles of the image transmitting optical system is fixed through the above-mentioned fixing member 254, is enclosed and fixed by a holding tube 260 and projects into the supporting barrel 257.

A lens barrel 261 is slidably provided within the supporting tube barrel 257.

An eyepiece 262 is held in this lens barrel 261 so that the image transmitted to the end surface of the image guide 225 through this eyepiece 262 may be observed from outside.

A visibility cam barrel 263 and visibility adjusting ring 237 are rotatably fitted in turn on the outer periphery of the above-mentioned supporting barrel 257. This visibility cam barrel 263 is provided with a visibility cam hole 264 on the peripheral wall.

Figure 38:
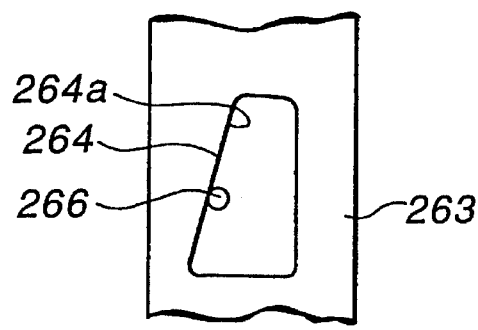

As shown in FIG. 38, the visibility cam hole 264 has a slope 264a.

The above-mentioned visibility adjusting ring 237 and visibility cam barrel 263 are integrally rotatably connected and fixed by a screw 265.

A lens pin 266 inserted through the visibility cam hole 264 is connected and fixed to the lens barrel 261. This lens pin 266 passes through the peripheral wall of a ring 267 loosely inserted in the part on the outer peripheral surface of the above-mentioned supporting barrel 257 to be integral with this ring 267.

A spring 268 is provided as compressed between the upper end surface of this ring 267 and the lower end surface of the large diameter part 256 of the above-mentioned supporting barrel 257.

Therefore, the lens barrel 261 holding the eyepiece 262 is energized through the ring 267 and lens pin 266 by the above-mentioned spring 268 so that this lens pin 266 may be in contact with the slope 264a of the visibility cam barrel 264 of the visibility cam barrel 263, as shown in FIG. 38.

According to this formation, when the visibility adjusting ring 237 is rotated, the visibility cam barrel 263 will rotate together with the visibility adjusting ring 237 and, therefore, the lens pin 266 in contact with the slope 264a of the visibility cam hole 264 of this visibility cam barrel 263 will move to the right and left in FIG. 38.

Therefore, as the lens barrel 261 holding the eyepiece 262 is operatively connected with the lens pin 266, the visibility can be adjusted.

Figure 39:
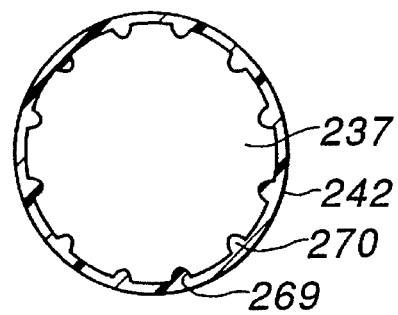

Here, as shown in FIG. 39, a plurality of grooves 269 are provided in the axial direction on the outer periphery of the visibility adjusting ring 237.

As shown in FIG. 39 which is a cross-sectional view taken along line D–D' in FIG. 36, projections 270 inside the eyepiece cap 242 are meshed with the grooves 269.

The eyepiece cap 242 and visibility adjusting ring 237 are integrated so that, when the eyepiece cap 242 is rotated, the visibility adjusting ring 237 will also rotate.

The visibility adjusting mechanism is not limited to be a ring but may be a lever.

The procedures from the fitting to inspection of the cover 2A in the eighth embodiment shall be explained below.

In FIG. 29, the cover holder 9 is covered with a cover holder cover (not illustrated) and then the endoscope operating part fixing mouth body part 18 of the cover 2A is set.

The switch of the cover expander 6 is engaged so that air may be fed from the open end of the expanding tube 32. The expanding tube 32 is fitted to the expanding tube mouth body 22 of the cover 2A.

Thus, air flows into the expanding groove 246 in FIG. 35, air is fed also into the adjacent endoscope inserting channel 34 and the endoscope inserting channel 34 inflates.

Here, the inserted part 11B of the cover endoscope 2B is inserted into the endoscope inserting channel 34. As the inserting channel has inflated, the inserted part 11B can be smoothly inserted and, even when the inserted part 11B is to be inserted, as the expanding groove 246 projects out of the endoscope channel 34, feeding air will not be obstructed.

As in FIG. 30, the tip part 19B of the inserted part 11B is set at the tip of the inserted part cover part 11A and the operating part 12B is also set. The expanding tube 32 is removed.

Then, the light guide cable 213B is inserted into the light guide cable inserting tube path 248 of the light guide cable cover part 213A. As a hole larger than the light guide cable 213B is made, it can be smoothly inserted. At this time, the connector 210 will project out of the light guide cable cover part 213A.

When the insertion ends, as the bridge cover 15A in FIG. 33 is connected at one end with the operating part cover part 12A and bridge 15 through the hinge and has the respective projection and recess at the other end, by only making the bridge cover 15A fall on the side of the operating part cover part 12A and bridge 15, both will be simply connected.

At this time, simultaneously, as shown in FIG. 39, the grooves 269 of the visibility adjusting ring 237 and the projections 270 of the eyepiece cap 242 will mesh with each other.

The connector 210 projecting out of the light guide cable cover part 213A is connected to the light source apparatus 3 and the air feeding tube path 26a, water feeding tube path 27a and sucking tube path 28a projecting in the same manner are connected to the fluid controlling apparatus 5 so that the endoscope inspection may be made.

In the endoscope inspection, to adjust the visibility, the eyepiece part 214 is seen through the transparent part of the eyepiece cap 242 shown in FIG. 36.

In case the visibility has deteriorated, the eyepiece cap 242 is rotated.

Then, as the projections 270 of the eyepiece cap 242 and the grooves 269 of the visibility adjusting ring 237 are meshed with each other as shown in FIG. 39, both will rotate integrally.

Then, in FIG. 37, the visibility adjusting ring 237 will rotate, the visibility cam barrel 263 will rotate together and the lens pin 266 in contact with the slope 264a of the visibility cam hole 264 of this visibility cam barrel 263 will move to the right and left in FIG. 38.

Therefore, as the lens barrel 261 holding the eyepieces 261 operatively connects with the lens pin 266, the visibility can be adjusted.

According to the eighth embodiment, the visibility can be adjusted as covered with the cover 2A.

The ninth embodiment shall be explained in the following. In this embodiment, only the eyepiece cap 242 in the eighth embodiment is modified but the others are the same and therefore the same components shall bear the same reference numerals and shall not be explained here.

Figure 40:
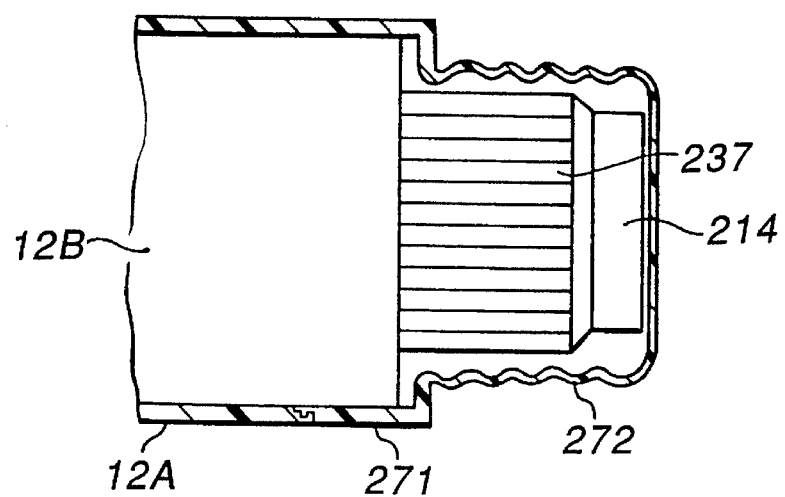
FIG. 40 is a cross-sectional view showing the vicinity of an eyepiece cap in the ninth embodiment of the present invention.

FIG. 40 is a cross-sectional view showing the essential parts of the ninth embodiment.

The operating part 12B is isolated from the external environment by the operating part cover part 12A and bridge cover 217 and the eyepiece part 214 is isolated from the external environment by the eyepiece cap 272 of an elastic material made of a transparent resin. Here, the bridge cover 271 and eyepiece cap 272 are integrally molded.

Here, the visibility adjusting ring 237 of the eyepiece part 214 of the eyepiece cap 272 is so soft as to be freely transformed in the resin and to be able to be held and rotated from outside the eyepiece cap 272.

The others are the same as in the eighth embodiment and therefore shall not be explained here. The operation shall be explained in the following.

In the endoscope inspection, the eyepiece part 214 is seen through the eyepiece cap 272.

In case the visibility has lagged, the visibility adjusting ring 237 of the eyepiece cap 272 is held and rotated. Here, the eyepiece cap 272 around the visibility adjusting ring 237 is made very soft that the visibility adjusting ring 237 can be held and rotated through the eyepiece cap 272.

When the visibility adjusting ring 237 is rotated, the visibility will be adjusted the same as in the eighth embodiment.

According to this embodiment, as the eyepiece cap 272 is made integral with the bridge cover 271, there is an effect that the cost is reduced.

The tenth embodiment shall be explained in the following. In this embodiment, an adjustment helping ring is added around the eyepiece cap of the ninth embodiment.

Figure 41:
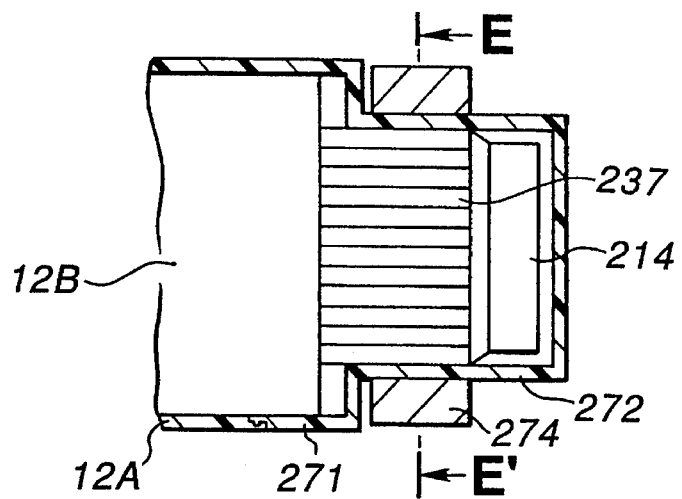
FIG. 41 is a cross-sectional view showing the vicinity of an eyepiece cap in the tenth embodiment of the present invention.

FIG. 41 is a cross-sectional view showing the tenth embodiment.

The operating part 12B is isolated from the external environment by the bridge cover 271 and the eyepiece part 214 is isolated from the external environment by the eyepiece cap 272 integral with the bridge cover 272. An adjustment helping ring 274 is fitted around the visibility adjusting ring 237 of the eyepiece cap 272.

Figure 42:
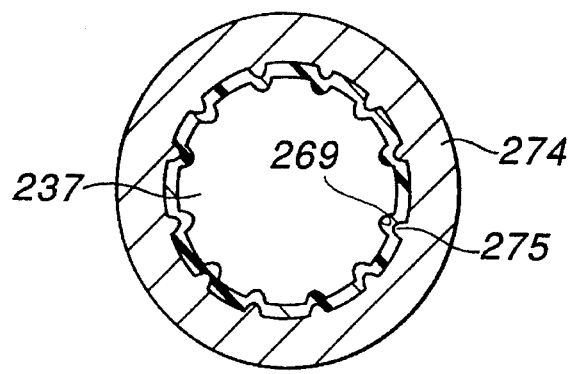
FIG. 42 is a cross-sectional view taken along line E–E' in FIG. 41.

As shown in FIG. 42 showing a section on line E–E' in FIG. 41, this adjustment helping ring 274 has projections 275 inside it which mesh with grooves 269 of the visibility adjusting ring 237 while transforming the eyepiece cap 272 of an elastic material.

When the adjustment helping ring 274 is rotated, the visibility adjusting ring 237 will also rotate.

The others are the same as in the ninth embodiment and therefore shall not be explained here. The operation is as follows.

In case the eyepiece cap 272 is seen to find that the visibility has lagged, the adjustment helping ring 274 is rotated.

Then, as the projections 275 inside the adjustment helping ring 274 mesh with the grooves 269 of the visibility adjusting ring 237, the visibility adjusting ring 237 will rotate to adjust the visibility.

In addition to the effect of the ninth embodiment, this tenth embodiment has an effect that the adjustment helping ring 274 located outside the cover is easy to rotate and serves to improve the operability.

The eleventh embodiment shall be explained in the following. In this embodiment, a focusing adjusting ring as added to the eyepiece part of the eighth embodiment. The features are the same as in the eighth embodiment.

Figure 43:
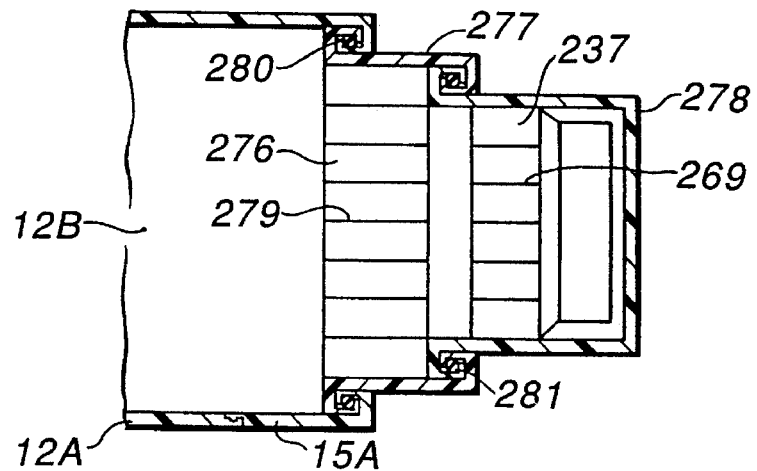
FIG. 43 is a cross-sectional view showing the vicinity of an eyepiece cap in the eleventh embodiment of the present invention.

FIG. 43 is a cross-sectional view showing the essential parts of the eleventh embodiment. A focusing lens 276 moving an objective lens at the tip of the inserted part (not illustrated) is rotatably provided in the operating part 12B.

In the focusing mechanism, a member to which an objective lens (not illustrated) is fixed at the tip is connected through a wire to the cam mechanism described in the eighth embodiment so as to be able to move in the axial direction within the insertable part.

There is a fine diameter part at the rear end of the focusing ring 276 and the visibility adjusting ring 237 is provided at its rear end.

The operating part 12B is covered with the bridge cover 14A, the focusing ring 276 is covered with the focus ring cover 277 and the visibility adjusting ring 237 is covered with the eyepiece cap 278. The focusing ring cover rotatably connects to the bridge cover 15A and the eyepiece cap 278 rotatably connects to the focusing ring cover 277.

Water-proofing O-rings 280 and 281 are provided in the respective connecting parts. The grooves 279 and 269 are provided respectively on the outer peripheries of the focusing ring 276 and the visibility adjusting ring 237 and mesh respectively with projections projected inside the focusing ring cover 277 and eyepiece cap 278.

When the focusing ring cover 277 is rotated, the focusing ring 279 will rotate and, when the eyepiece cap 278 is rotated, the visibility adjusting ring 237 will rotate.

In this embodiment, when the eyepiece cap 278 is rotated the visibility adjusting ring 237 will rotate and the visibility will be adjusted and, when the focusing ring cover 277 is rotated, the focusing ring 276 wil rotate and the focus will be adjusted.

According to this embodiment, there is an effect that the focusing mechanism is added to the effect of the eighth embodiment and the operability further improves.

The focusing mechanism can also be applied, for example, to the cover endoscope 28 provided with the CCD 25 of the first embodiment. Further, the objective optical system may be formed to be, for example, a zooming optical system so that the zooming optical system may be moved in the optical axis direction by a wire advancing and retreating operation to obtain a magnified observed image.

Different embodiments can be formed by combining various portions of the above-described first to eleventh embodiments and they also belong to the present invention.

What is claimed is:

1. An endoscope cover system endoscope comprising:

an endoscope having an elongate inserted part provided with a curvable curving part and an operating part provided with a curving operating means for curvably operating said curving part;

a channeled endoscope cover having an inserted part cover part provided with an endoscope inserting channel through which said inserted part is inserted and a fluid tube path through which a fluid flows; and a twisting and curving means for, when said curving part is curved close to the maximum curvature angle in the maximum curvature angle direction by operating said curving operating means, curving and twisting the fluid tube path within said inserted part cover part so as to move outside the maximum curvature angle direction.

2. An endoscope cover system endoscope comprising:

an endoscope having an elongate inserted part provided with a curvable curving part and an operating part provided with a curving operating means for curvably operating said curving part;

a channeled endoscope cover having an inserted part cover part provided with an endoscope inserting channel through which said inserted part is inserted and a fluid tube path through which a fluid flows; and a twisting and curving means for, when said curving part is curved close to the maximum curvature angle in the maximum curvature angle direction in the direction of the curvature highest in the using frequency by operating said curving operating means, curving and twisting the fluid tube path within said inserted part cover part so as to move outside the maximum curvature angle direction.

3. An endoscope cover system endoscope comprising:

an endoscope having an elongate inserted part provided with a curvable curving part and an operating part provided with a curving operating means for curvably operating said curving part;

a channeled endoscope cover having an inserted part cover part provided with an endoscope inserting channel through which said inserted part is inserted; and a fluid tube path which is arranged on the side avoiding the maximum curvature angle direction of said curving part within said inserted part cover part and through which a fluid flows, wherein the flexibility around said fluid tube path in said inserted part cover part is less than the flexibility around said endoscope inserting channel.

4. An endoscope cover system endoscope comprising:

an endoscope having an elongate inserted part provided with a curvable curving part and an operating part provided with a curving operating means for curvably operating said curving part;

a channeled endoscope cover having an inserted part cover part provided with an endoscope inserting channel through which said inserted part is inserted; and a fluid tube path which is arranged on the side avoiding the curvature angle direction highest in the using frequency within said inserted part cover part and through which a fluid flows, wherein the flexibility around said fluid tube path in said inserted part cover part is made smaller than the flexibility around said endoscope inserting channel.

5. An endoscope cover system endoscope according to claim 1, 2, 3 or 4, wherein said channeled endoscope cover has an operating part cover part covering said operating part and said operating part cover part and said inserted part cover part are separable from each other.

6. An endoscope cover system endoscope according to claim 1, 2, 3 or 4, wherein said channeled endoscope cover has an operating part cover part covering said operating part, said curving operating means has a curving operating knob having a rotatable shaft and said operating part cover part is separable at an opening passing through said shaft.

7. An endoscope cover system endoscope comprising:

an endoscope having an elongate inserted part provided with a curvable curving part having adjacent curving pieces rotatably connected to each other through pivoting members and a curving wire fixed at one end near the foremost curving piece and an operating part provided with a curving operating means for curvably operating said curving part by pulling said curving wire;

a channeled endoscope cover having an inserted part cover part provided with an endoscope inserting channel through which said inserted part is inserted; and a fluid tube path which is arranged on the side avoiding the curving direction becoming the maximum curvature angle within said inserted part cover part and through which a fluid flows, wherein the supporting position in the peripheral direction in said foremost curving piece of said curving wire and the tension acting on said curving wire are so determined that the second moment acting in the direction separating from said fluid tube path may be larger than the first moment generated in said foremost curving piece and acting toward said fluid tube path side.

8. An endoscope cover system endoscope comprising:

an endoscope having an elongate inserted part provided with a curvable curving part having adjacent curving pieces rotatably connected with each other through pivoting members and a curving wire fixed at one end near the foremost curving piece and an operating part provided with a curving operating means for curvably operating said curving part by pulling said curving wire;

a channeled endoscope cover having an inserted part cover part provided with an endoscope inserting channel through which said inserted part is inserted; and a fluid tube path which is arranged on the side avoiding the curvature angle direction highest in the using frequency within said inserted part cover part and through which a fluid flows, wherein the supporting position in the peripheral direction in said foremost curving piece of said curving wire and the tension acting on said curving wire are so determined that the second moment acting in the direction separating from said fluid tube path may be larger than the first moment generated in said foremost curving piece and acting toward said fluid tube path side.

9. An endoscope cover system endoscope comprising:

an endoscope having an elongate inserted part provided with a curvable curving part having adjacent curving pieces rotatably connected with each other through pivoting members and a curving wire fixed at one end near the foremost curving piece and an operating part provided with a curving operating means for curvably operating said curving part by pulling said curving wire; and a channeled endoscope cover having an endoscope inserting channel which is arranged in the curving direction becoming the maximum curvature angle or on one side of the opposite side and through which said inserted part is inserted and a fluid tube path housing channel which is arranged on the other side and houses a plurality of fluid tube paths through which a fluid flows, wherein the fluid tube path of the maximum inside diameter in said plurality of fluid tube paths is arranged on the side most separated from the curving direction side on which said maximum curvature angle is generated.

10. An endoscope cover system endoscope comprising:

an endoscope having an elongate inserted part provided with a curvable curving part having adjacent curving pieces rotatably connected with each other through pivoting members and a curving wire fixed at one end near the foremost curving piece and an operating part provided with a curving operating means for curvably operating said curving part by pulling said cutting wire; and a channeled endoscope cover having an endoscope inserting channel which is arranged on the side in which the curving direction is highest in the using frequency and through which said inserted part is inserted and a fluid tube path housing channel which is arranged on the other side and which houses a plurality of fluid tube paths through which a fluid flows, wherein the fluid tube path of the maximum inside diameter in said plurality of fluid tube paths is arranged on the side separating in the direction at right angles with the curving direction highest in the using frequency.

11. An endoscope cover system endoscope comprising:

an endoscope having an elongate inserted part provided with a curvable curving part formed by rotatably connecting adjacent curving pieces with each other through pivoting members and an operating part provided with a curving operating means curving operating said curving part; and a channeled endoscope cover having an endoscope inserting channel through which said inserted part is inserted and a fluid tube path through which a fluid flows, wherein, by said curving operation, said fluid tube path is arranged in the direction intersecting substantially at right angles with the maximum curvature angle direction in which the maximum curvature angle is generated and the difficulty in curving said inserted part cover part is greater on the side on which said fluid tube path is arranged than on the side on which said fluid tube path is not arranged.

12. An endoscope cover system endoscope comprising:

an endoscope having an elongate inserted part provided with a curving part wherein adjacent curving pieces are rotatably connected with each other through a pair of first pivoting members opposed to each other, the maximum curvature angle direction in which the maximum curvature angle is made around the first axis passing through said first pivoting member is set and the adjacent curving pieces are rotatably connected with each other through a pair of second pivoting members intersecting substantially at right angles with said first pivoting members and become curvable also around the second axis passing through said second pivoting members and an operating part provided with a curving operating means for curvably operating said curving part; and a channeled endoscope cover having an inserted part cover part in which are arranged an endoscope inserting channel through which said inserted part is inserted and a fluid tube path through which a fluid will flow to one side of said second axis in case said inserted part is inserted through said endoscope inserting channel, wherein the difficulty in curving said inserted part cover part on both sides of said second axis is made larger on the side on which said fluid tube path is arranged than on the side on which said fluid tube path is not arranged.

13. An endoscope cover system endoscope comprising:

an endoscope having an elongated inserted part provided with a curvable curving part and an operating part provided removably with a curving operating means for curvably operating said curving part;

a channeled endoscope cover having an inserted part cover part provided with an endoscope inserting channel through which said inserted part is inserted and an operating part cover part covering said operating part;

an opening provided in said operating part cover part and for fitting said curving operating member to said operating part from outside said operating part cover part; and a plurality of switches provided in said operating part and required to be operated to separate said curving operating member from said operating part.

* * * * *